United States Patent
Findikoglu et al.

(10) Patent No.: US 10,585,069 B2
(45) Date of Patent: Mar. 10, 2020

(54) DETECTION, MONITORING, AND DETERMINATION OF LOCATION OF CHANGES IN METALLIC STRUCTURES USING MULTIMODE ACOUSTIC SIGNALS

(71) Applicants: Chevron U.S.A. Inc., San Ramon, CA (US); TRIAD NATIONAL SECURITY, LLC, Los Alamos, NM (US)

(72) Inventors: Alp T. Findikoglu, Santa Fe, NM (US); Dipen N. Sinha, Los Alamos, NM (US); Daniel R. Chapman, Oakland, CA (US)

(73) Assignees: Chevron U.S.A. Inc., San Ramon, CA (US); Triad National Security, LLC, Los Alamos, NM (US)

(*) Notice: Subject to any disclaimer, the term of this patent is extended or adjusted under 35 U.S.C. 154(b) by 28 days.

(21) Appl. No.: 15/964,967

(22) Filed: Apr. 27, 2018

(65) Prior Publication Data
US 2018/0292356 A1 Oct. 11, 2018

Related U.S. Application Data

(63) Continuation-in-part of application No. 15/751,429, filed as application No. PCT/US2016/046919 on Aug. 12, 2016, now Pat. No. 10,473,625.
(Continued)

(51) Int. Cl.
*G01N 29/44* (2006.01)
*G01N 29/34* (2006.01)
(Continued)

(52) U.S. Cl.
CPC ........... *G01N 29/043* (2013.01); *G01N 29/07* (2013.01); *G01N 29/343* (2013.01);
(Continued)

(58) Field of Classification Search
CPC .... G01N 29/043; G01N 29/348; G01N 29/42; G01N 29/449; G01N 29/4409;
(Continued)

(56) References Cited

U.S. PATENT DOCUMENTS 4,623,468 A * 11/1986 Lepain .................... C02F 1/682
                                                          210/749
4,890,055 A    12/1989 Van Broekhoven
(Continued)

FOREIGN PATENT DOCUMENTS

WO     2017099852     6/2017

*Primary Examiner* — Suman K Nath
(74) *Attorney, Agent, or Firm* — Esplin & Associates, PC

(57) ABSTRACT

Methods for detection, monitoring, and determination of location of changes in rigid structures with arbitrarily complex geometries are described. Implementations include locating acoustic transducers that generate and receive acoustic signals at multiple locations along a surface of the rigid structure, wherein longitudinal spacing between the transducer locations define measurement zones. Acoustic signals with chosen amplitude-time-frequency characteristics excite multiple vibration modes in the structure within each zone. Small mechanical changes in the inspection zones lead to scattering and attenuation of broadband acoustic signals, which are detectable as changes in received signal characteristics as part of a through-transmission technique. Additional use of short, narrowband pulse acoustic signals as part of a pulse-echo technique allows determination of the relative location of the mechanical change within each zone based on the differential delay profiles.

20 Claims, 26 Drawing Sheets

Related U.S. Application Data

(60) Provisional application No. 62/204,222, filed on Aug. 12, 2015.

(51) Int. Cl.
    *G01N 29/46*     (2006.01)
    *G01N 29/04*     (2006.01)
    *G01N 29/07*     (2006.01)
    *G01N 29/42*     (2006.01)

(52) U.S. Cl.
    CPC .......... *G01N 29/348* (2013.01); *G01N 29/42* (2013.01); *G01N 29/449* (2013.01); *G01N 29/4409* (2013.01); *G01N 29/4463* (2013.01); *G01N 29/4472* (2013.01); *G01N 29/46* (2013.01); *G01N 2291/011* (2013.01); *G01N 2291/0258* (2013.01); *G01N 2291/048* (2013.01); *G01N 2291/0425* (2013.01); *G01N 2291/102* (2013.01); *G01N 2291/2634* (2013.01)

(58) Field of Classification Search
    CPC .. G01N 29/4472; G01N 29/46; G01N 29/343; G01N 29/4463; G01N 29/07; G01N 2291/102; G01N 2291/048; G01N 2291/0425; G01N 2291/2634; G01N 2291/011; G01N 2291/0258
    USPC ............................ 73/592, 40.5 R, 49.1, 49.5
    See application file for complete search history.

(56) References Cited

U.S. PATENT DOCUMENTS

| | | | |
|---|---|---|---|
| 5,526,689 A | 6/1996 | Coulter | |
| 5,987,990 A * | 11/1999 | Worthington | G01N 29/14 |
| | | | 73/40.5 A |
| 7,307,914 B1 | 12/2007 | Carter | |
| 8,225,665 B2 | 7/2012 | Geir | |
| 9,632,062 B2 * | 4/2017 | Tanaka | G01N 29/043 |
| 2007/0017800 A1 | 1/2007 | Cetinkaya | |
| 2007/0072137 A1 | 3/2007 | Peluso | |
| 2009/0150094 A1 | 6/2009 | Van Velsor | |
| 2010/0079258 A1 | 4/2010 | Ihn | |
| 2010/0278008 A1 | 11/2010 | Ammar | |
| 2011/0301882 A1 | 12/2011 | Andersen | |
| 2012/0055253 A1 | 3/2012 | Sinha | |
| 2012/0055264 A1 | 3/2012 | Sinha | |
| 2015/0053009 A1 | 2/2015 | Yan | |
| 2015/0212048 A1 * | 7/2015 | Ganesan | G01B 17/00 |
| | | | 73/632 |
| 2018/0292356 A1 | 10/2018 | Findikoglu | |

* cited by examiner

DETECTION, MONITORING, AND DETERMINATION OF LOCATION OF CHANGES IN METALLIC STRUCTURES USING MULTIMODE ACOUSTIC SIGNALS

CROSS-REFERENCE TO RELATED APPLICATIONS

The present application is a continuation-in-part of U.S. patent application Ser. No. 15/751,429 for "Detection and Monitoring of Changes in Metallic Structures Using Multimode Acoustic Signals" which was filed on Feb. 8, 2018, which is a National Stage Entry of PCT/US16/46919, filed Aug. 12, 2016, which claims the benefit of U.S. Provisional Patent Application No. 62/204,222, which was filed on Aug. 12, 2015, the entire contents of which are hereby incorporated herein by reference.

ACKNOWLEDGEMENT OF GOVERNMENT SUPPORT

This invention was made with government support under Contract No. DE-AC52-06NA25396 awarded by the U.S. Department of Energy. The government has certain rights in the invention.

PARTIES TO JOINT RESEARCH AGREEMENT

The research work described here was performed under a Cooperative Research and Development Agreement (CRADA) between Los Alamos National Laboratory (LANL) and Chevron under the LANL-Chevron Alliance, CRADA number LA05C10518.

FIELD

The present disclosure relates generally to the detection of and monitoring of changes in mechanical structures, pipes, vessels, and storage containers and, more particularly, to the use of multimode acoustic signal propagation and signal detection for detecting and monitoring changes in mechanical structures, and in walls of pipes, vessels, and storage containers.

BACKGROUND

Detection of and monitoring of material loss due to pitting, cracking and fractures, material conversion from corrosion and/or erosion, and material addition from material migration and accumulation, and material adsorption, as examples, in mechanical structures, and walls of pipes, vessels, and storage tanks in hard-to-access environments, such as under insulation or under paint, are important in many industries that involve liquid or gas storage and flow.

The detection of corrosion under insulation is done most effectively by visual inspection by removing the insulation, which is time consuming and costly. Other methods of detection include radiography, eddy current techniques, x-ray, remote TV monitoring, electromagnetic devices, local acoustic interrogation, and long-range acoustic interrogation using an array of acoustic transducers. These methods are not widely used because the information provided has too limited a range to be of practical value, or the apparatus involved is too cumbersome or expensive to implement. Moreover, existing methods for detecting anomalies in rigid structures are not capable of determining a particular location of the anomaly within a zone of interest.

BRIEF SUMMARY

One aspect of the present disclosure relates to a method for detection and monitoring of a mechanical change in an elongated rigid structure. In some examples, a particular location of a mechanical change or anomalous feature within a zone identified on a rigid structure may be determined by using a joint through-transmission/pulse-echo technique in two stages, whereby the originating vibrational signals are propagated in opposing directions (i.e., into two neighboring zones) from an initiating transducer and received by two receiving transducers/sensors. In the first stage, the magnitude of changes and spectral response of the structure in two neighboring zones are determined using a through-transmission method. For some applications, the first stage is sufficient to detect and monitor a mechanical change in a zone of an elongated structure, without the need for information on the specific location and extent of the change within the zone. In the second stage, using the information gained in the first-stage measurement, a mono-tone pulse at a specific frequency with a certain time duration is employed in a pulse-echo method, from which spatial information of the changes within either zone is deduced. The received signals may be analyzed to determine differential changes by subtracting previously-recorded baseline signals from received signals. The differential changes may be used to determine if either zone contains a mechanical change, and if so, to determine the location of the mechanical change within the applicable zone.

In some examples, the rigid elongated structure may be fabricated from or include metal. The rigid elongated structure may be a pipe, frame, crane, beam, mechanical support, or other rigid structure as known in the art. In some examples, a method for identifying the location of an anomalous feature along a rigid structure may include locating acoustic transducers along the surface of a rigid structure configured to transmit broadband and narrow band acoustic signals along the rigid structure. The acoustic transducers may also be configured to receive resulting transmitted and reflected or scattered response signals along the rigid structure generated in response to the broadband and/or narrow band acoustic signals. In some examples, three such acoustic transducers may be located along the rigid structure as to define two neighboring zones. For example, the method may include locating a first acoustic transducer, a second acoustic transducer, and a third acoustic transducer along the rigid structure, with the second acoustic transducer located between the first acoustic transducer and the third acoustic transducer as to define a first zone and the second zone. For example, a longitudinal spacing between the first location and the second location may define the first zone. A longitudinal spacing between the second location and the third location may define the second zone.

In some embodiments, the method may include generating, with the second acoustic transducer, a baseline broadband acoustic signal along the rigid elongated structure. The method may include obtaining, with the first acoustic transducer, a first baseline transmission signal responsive to the baseline broadband acoustic signal in the first zone. The method may include obtaining, with the third acoustic transducer, a second baseline transmission signal responsive to the baseline broadband acoustic signal in the second zone. The method may include generating, with the second acoustic transducer, a monitoring broadband acoustic signal along the rigid elongated structure. The method may include obtaining, with the first acoustic transducer, a first monitoring transmission signal responsive to the monitoring broadband acoustic signal in the first zone. In some embodiments, the method may include obtaining, with the third acoustic transducer, a second monitoring transmission signal responsive to the monitoring transmission signal in the second zone.

The method may include determining a first differential transmission signal as a difference between the first monitoring transmission signal and the first baseline transmission signal. The method may include determining a second differential transmission signal as a difference between the second monitoring transmission signal and the second baseline transmission signal. The method may include determining if the mechanical change occurred in the first zone of the elongated rigid structure based on the first differential transmission signal or if the mechanical change occurred in the second zone of the elongated rigid structure based on the second differential transmission signal.

In some implementations, the method may further include generating, with the second acoustic transducer, a baseline narrow-band pulse acoustic signal along the elongated rigid structure. The method may further include obtaining, with the first acoustic transducer, a first baseline response signal responsive to the baseline narrow-band pulse acoustic signal in the first and second zones. The method may further include obtaining, with the third acoustic transducer, a second baseline response signal responsive to the baseline narrow-band pulse acoustic signal in the second and first zones. The method may further include generating, with the second acoustic transducer, a monitoring narrow-band pulse acoustic signal along the elongated rigid structure. The method may further include obtaining, with the first acoustic transducer, a first monitoring response signal responsive to the baseline narrow-band pulse acoustic signal in the first and second zones. The method may further include obtaining, with the third acoustic transducer, a second monitoring response signal responsive to the baseline narrow-band pulse acoustic signal in the second and first zones.

In some examples, the method may include determining a first differential response signal as a difference between the first monitoring response signal and the first baseline response signal. The method may further include determining a second differential response signal as a difference between the second monitoring response signal and the second baseline response signal. The method may further include generating a first differential delay profile as a function of the first differential response signal as compared with the second differential response signal. The method may further include generating a second differential delay profile as a function of the second differential response signal as compared with the first differential response signal. The method may further include determining the relative location of the mechanical change within the first zone or the second zone based on the first differential delay profile and the second differential delay profile.

In some implementations, the first and third acoustic transducers may each include an acoustic sensor configured to detect an acoustic signal. In some implementations, the second acoustic transducer may include an acoustic transmitter configured to generate an acoustic signal.

In some implementations, the method may include normalizing the first monitoring transmission signal to the first baseline transmission signal, whereby maximum values of the first baseline transmission signal and the first monitoring transmission signal are less than or equal to a first selected value. The method may further include performing short-time Fourier Transforms of the first baseline and first monitoring transmission signals using a selected time window size, a selected frequency window size, and a selected time step. The method may further include calculating a first difference between the normalized first monitoring transmission signal and the normalized first baseline transmission signal, forming thereby a first two-dimensional contour map. The method may further include identifying a first frequency-time mode pair in the first two-dimensional contour map, where one feature of the first frequency-time mode pair has a first maximum positive value and the corresponding feature of the first frequency-time mode pair has a first maximum negative value.

In some implementations, the method may further include normalizing the second monitoring transmission signal to the second baseline transmission signal, whereby maximum values of the second baseline transmission signal and the second monitoring transmission signal are less than or equal to a second selected value. The method may further include performing short-time Fourier Transforms of the second baseline and second monitoring transmission signals using the selected time window size, the selected frequency window size, and the selected time step. The method may further include calculating a second difference between the normalized second monitoring transmission signal and the normalized second baseline transmission signal, forming thereby a second two-dimensional contour map. The method may further include identifying a second frequency-time mode pair in the second two-dimensional contour map, where one feature of the second frequency-time mode pair has a second maximum positive value and the corresponding feature of the second frequency-time mode pair has a second maximum negative value.

In some implementations, the method may further include displaying the first and the second two-dimensional contour maps on a graphical user interface. In some examples, the method may further include identifying, with a graphical user interface, the selected time window size, the selected frequency window size, and the selected time step. In some implementations, a size of the first zone is about a size of the second zone.

The elongated rigid structure may be fabricated from a rigid material such as metal. In some examples, the elongated rigid structure comprises a pipe, a pipe assembly, a flange, an elbow, a tee, a reducer, a weld, a vessel, a storage tank, or a storage container. In some implementations, the method may further include filtering the first and second monitoring transmission signals. For example, the baseline and monitoring broadband acoustic signals each have a frequency of between about 1 kHz and about 1 MHz.

In some implementations, the method may further include generating multiple baseline broadband acoustic signals along the rigid elongated structure. The method may include obtaining multiple first baseline transmission signals responsive to the baseline broadband acoustic signals in the first zone and multiple second baseline transmission signals responsive to the baseline broadband acoustic signals in the second zone. The method may further include for a baseline condition when no mechanical change is present in either the first zone or the second zone, averaging a selected number of first baseline transmission signals and averaging a selected number of second baseline transmission signals. The method may further include removing DC components from the averaged first baseline transmission signals and the averaged second baseline transmission signals.

In some implementations, the method may include generating a set of temperature-compensated monitoring transmission signals by performing temperature compensation of the first monitoring transmission signal and the second monitoring transmission signal as compared with the first baseline transmission signal and the second baseline transmission signal.

In some implementations, the method may further include dividing the first and second monitoring transmission signals into a selected number of equal-duration time bins as a function of time. The method may further include calculating a cross-correlation function for the first and second monitoring transmission signals and the first and second baseline transmission signals within a time bin. The method may further include determining a time shift for the time bins by locating a peak of the cross correlation function. The method may further include assigning a value of the first and second monitoring transmission signals to a time bin corresponding to a value of the first or second baseline transmission signals at a corresponding time shifted time bin.

Another aspect of the present disclosure relates to a method for detecting and monitoring of an anomalous feature in an elongated rigid structure. The method may include locating a first acoustic transducer at a first location along a surface of the rigid structure. The method may include locating a second acoustic transducer at a second location along the surface of the rigid structure. The method may include locating a third acoustic transducer at a third location along the surface of the rigid structure, wherein the second location is between the first location and the third location, a longitudinal spacing between the first location and the second location define a first zone, and a longitudinal spacing between the second location and the third location define a second zone. The method may include generating, with the second acoustic transducer, multiple broadband acoustic signals along the rigid elongated structure. The method may include obtaining, with the first acoustic transducer and the second acoustic transducer, multiple transmission signals responsive to the broadband acoustic signals. The method may include determining if an anomalous feature exists in the first zone or the second zone based on a detected change in the transmission signals. The method may include generating, with the second acoustic transducer, multiple narrow-band signals along the elongated rigid structure. The method may include obtaining, with the first acoustic transducer, a first baseline response signal and a first monitoring response signal responsive to the narrow-band signals. The method may include obtaining, with the third acoustic transducer, a second baseline response signal and a second monitoring response signal responsive to the monitoring narrow-band signals. The method may include generating, with a delay profile generation logical circuit and/or algorithm, multiple differential delay profiles as a function of differences between the first and second baseline response signals and the first and second monitoring response signals. The method may include determining the relative location of the mechanical change within the first zone or the second zone based on the differential delay profiles.

In some implementations, obtaining the first and second baseline response signals may occur during a baseline condition in which no detectable anomalous feature is present in either the first zone or the second zone of the elongated rigid structure. For example, obtaining the first and second monitoring response signals occurs after obtaining the first and second baseline response signals.

In some implementations, the method may include determining a first differential response signal as a difference between the first monitoring response signal and the first baseline response signal. The method may further include determining a second differential response signal as a difference between the second monitoring response signal and the second baseline response signal. The method may further include generating a first differential delay profile as a function of the first differential response signal as compared with the second differential response signal. The method may further include generating a second differential delay profile as a function of the second differential response signal as compared with the first differential response signal.

Displaying the differential delay profiles may include presenting graphical plots on a graphical user interface. The narrow-band acoustic signals may be Gaussian-enveloped pulses.

In some implementations, more than one transmitting sensor could be employed concurrently to improve signal strength, and consequently signal-to-noise ratio in the measurement. Multiple transmitting sensors could be located in close proximity to each other, or distributed across an extended area. In the case of distributed multiple sensors, the transmitted signals could be more evenly distributed across the extended structure, thereby improving the detection of mechanical changes or anomalous features in complex geometries. The receiving sensors would perform similarly to above descriptions. Signal analyses, such as normalization, difference taking, temperature compensation, Fourier transforms, etc., could also be performed similarly.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as limiting. As used in the specification and in the claims, the singular form of "a", "an", and "the" include plural referents unless the context clearly dictates otherwise.

BRIEF DESCRIPTION OF THE DRAWINGS

The accompanying drawings, which are incorporated in and form a part of the specification, illustrate the embodiments of the present disclosure and, together with the description, serve to explain the principles of the disclosed technology. In the drawings:

FIG. 1A is a schematic representation of an embodiment of the basic apparatus suitable for practicing embodiments of the method of the disclosed technology showing a linear pipe section, while

Figure 2:
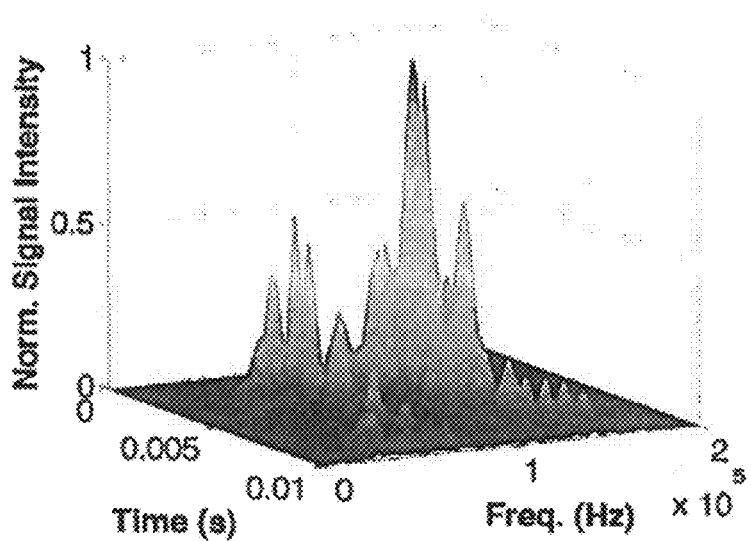
FIG. 2 shows the received signal after a linear chirp was transmitted 20-ft along an empty corroded pipe having 10-in. diameter, and ½-in. wall thickness.
Figure 3:
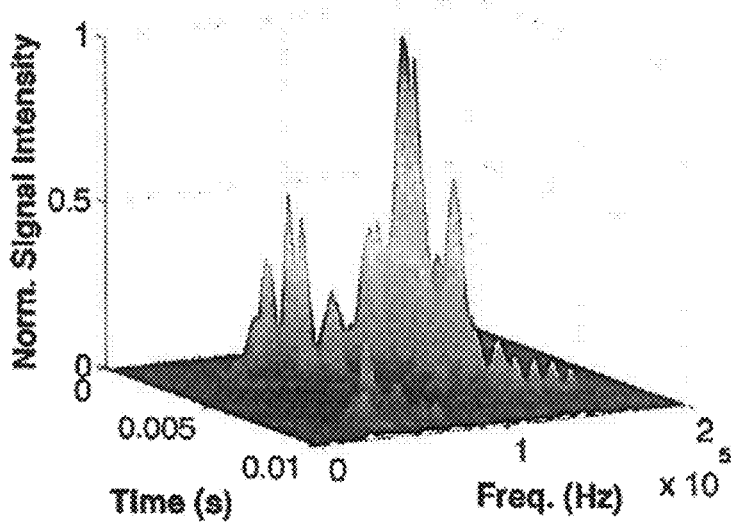
FIG. 3 shows the same received signal after a linear chirp signal was transmitted 20-ft along the empty corroded pipe described in FIG. 2, hereof, but perturbed by attaching, 12 small magnets on the pipe wall, thereby generating a local volume change of about 3% on the pipe wall.
Figure 4A:
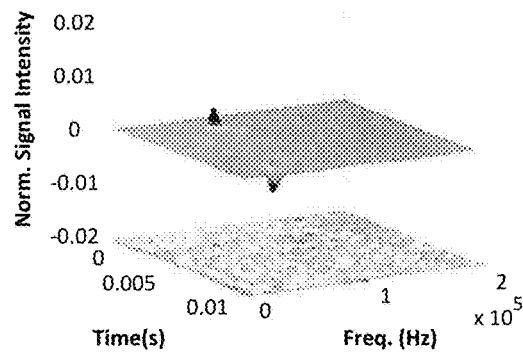
Figure 4B:
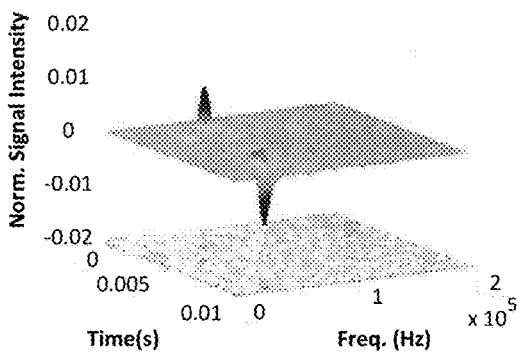
Figure 4C:
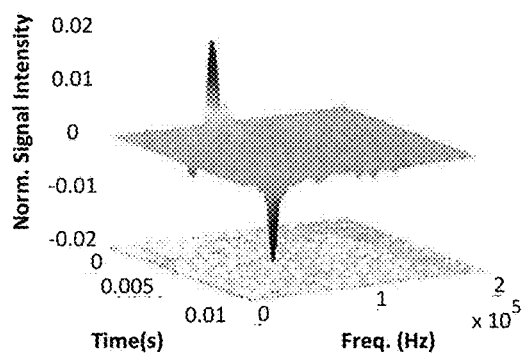

FIGS. 4A-4C are graphs of the Normalized-Difference Short-Time-Fourier-Transform (ND-STFT) signal calculated by taking the difference between the first (baseline) and the second (perturbed) signal intensities shown in FIGS. 2 and 3, hereof, for 2, 4 and 12 attached magnets, respectively.

Figure 5:
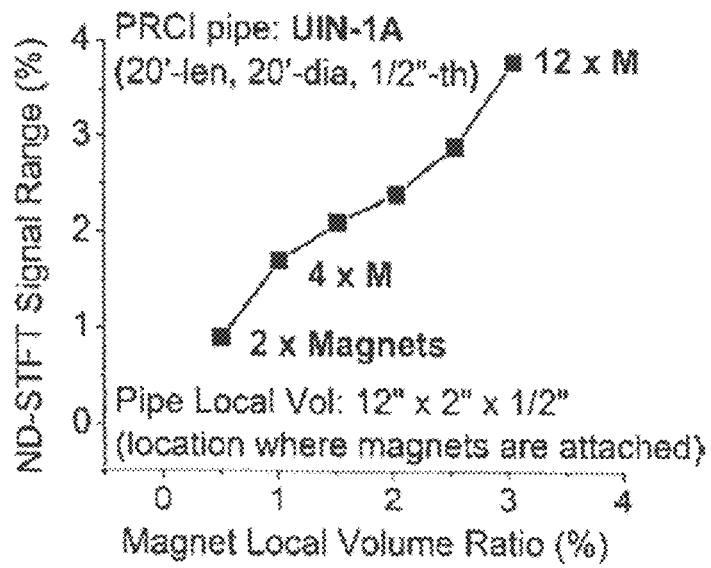

FIG. 5 is a graph of the difference of the maximum height and the minimum depth in the ND-STFT map, as a function of magnets attached.

Figure 6:
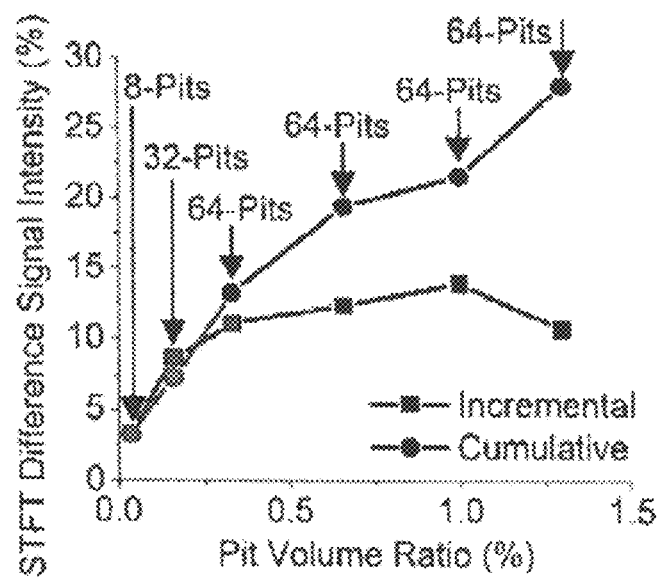

FIG. 6 is a graph of the difference in the maximum height and the minimum depth in the ND-STFT map (that is, the maximum signal difference), or, equivalently, the STFT difference signal intensity, as a function of material removed (or, pit volume ratio) for a signal having travelled along an uncorroded pipe having 20-ft. length, 2¾-in. diameter, and ¼-in. wall thickness.

Figure 7:
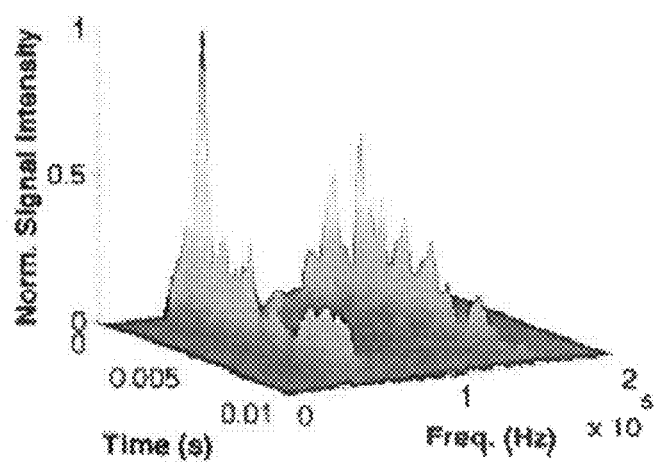

FIG. 7 is a graph of the received signal with no perturbation (baseline) having travelled the length of a cylindrical vessel, wherein 4 transmitting transducers and 1 receiving transducer are employed.

Figure 8A:
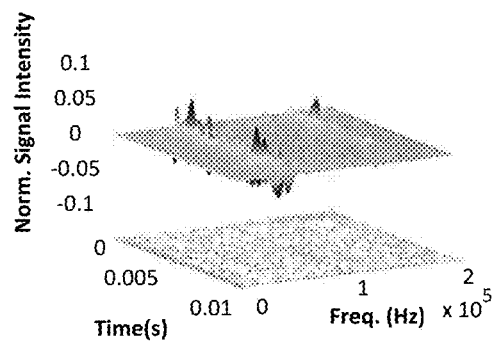
Figure 8B:
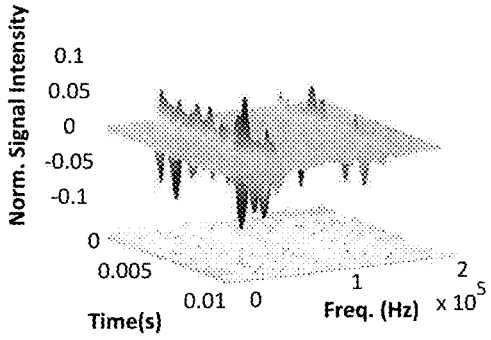
Figure 8C:
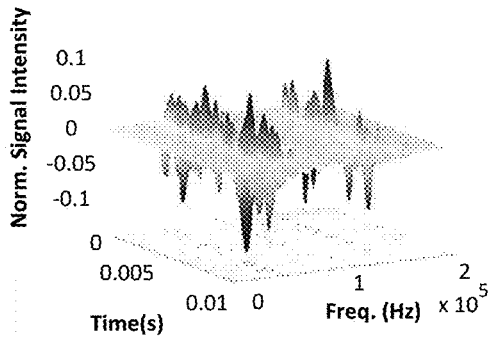

FIGS. 8A-8C are graphs of the ND-STFT difference signal between the baseline and after 0.2 cc, 0.6 cc and 1.2 cc of material, respectively, was removed by grinding.

Figure 9:
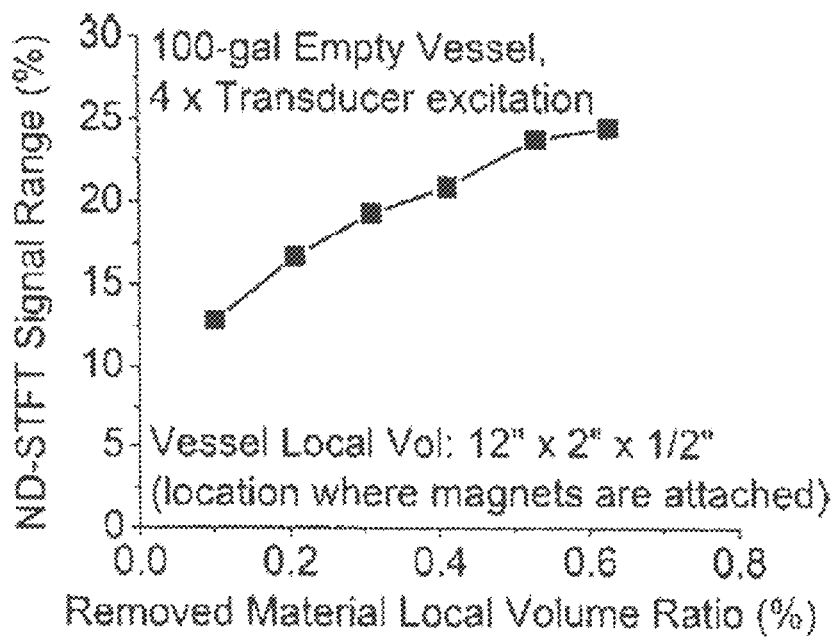

FIG. 9 is a graph of the maximum height and the minimum depth of the ND-STFT map (i.e., maximum signal difference), as a function of removed material from an empty vessel.

Figure 10:
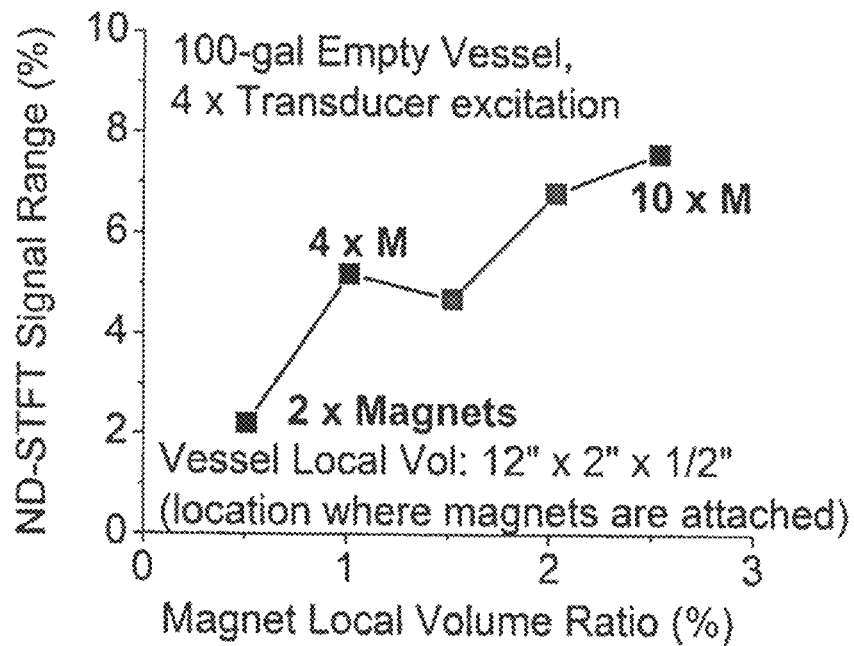

FIG. 10 is a graph of the difference between the maximum height and the minimum depth of the ND-STFT map (that is, the maximum signal difference), as a function of added material (magnets) for an empty vessel.

Figure 11A:
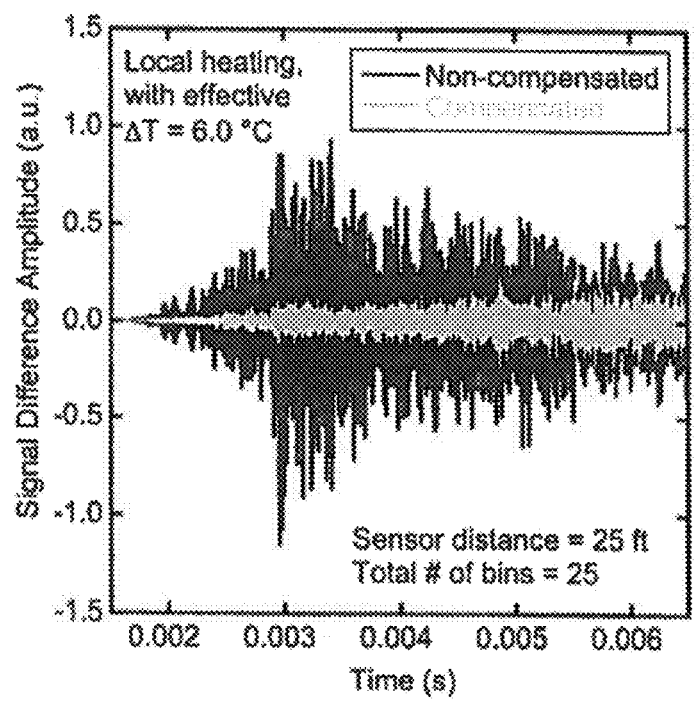
Figure 11B:
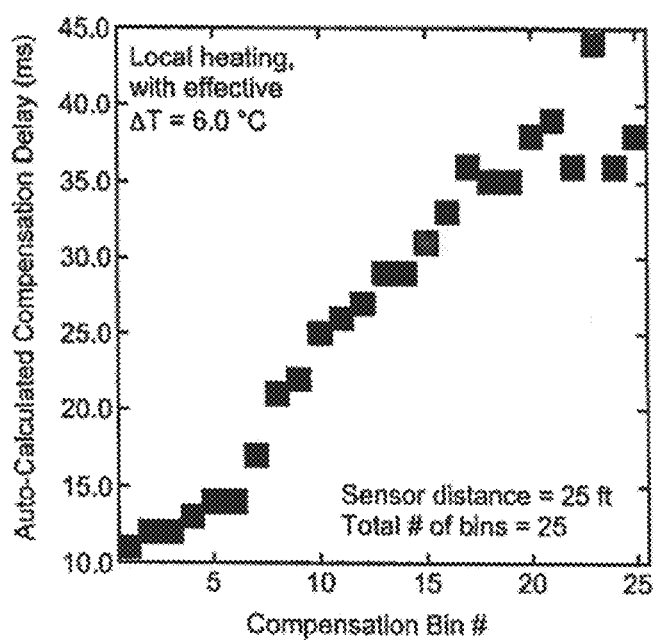

FIG. 11A is a graph of the signal difference amplitude as a function of time for both temperature compensated and non-temperature-compensated signals for a 25 ft. section of a 105-ft long pipe assembly, while FIG. 11B is a graph illustrating the specific delay times that are calculated for each bin (for a total of 25 bins) for the data shown in FIG. 11 A.

Figure 12A:
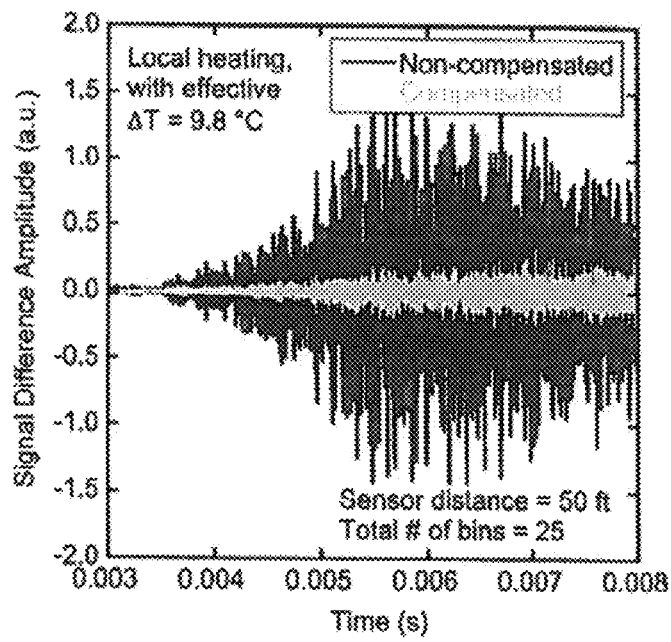
Figure 12B:
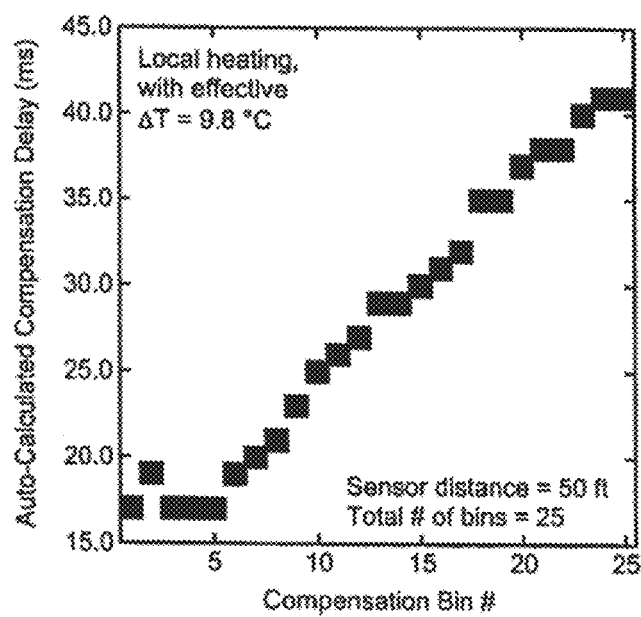

FIG. 12A is a graph of the signal difference amplitude as a function of time for both temperature compensated and non-temperature-compensated signals for a 50 ft. section of a 105-ft long pipe assembly, while FIG. 12B is a graph illustrating the specific delay times that are calculated for each bin (for a total of 25 bins) for the data shown in FIG. 12A.

Figure 13A:
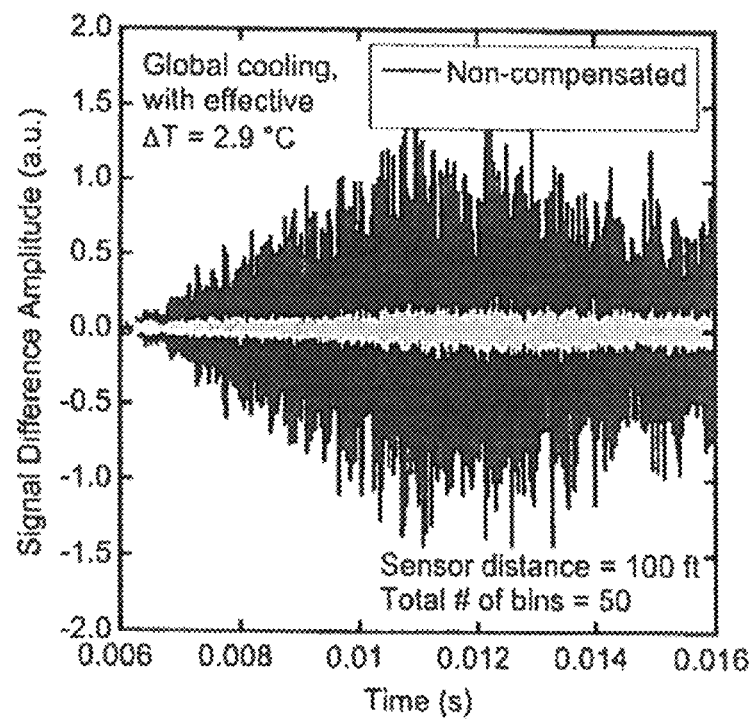
Figure 13B:
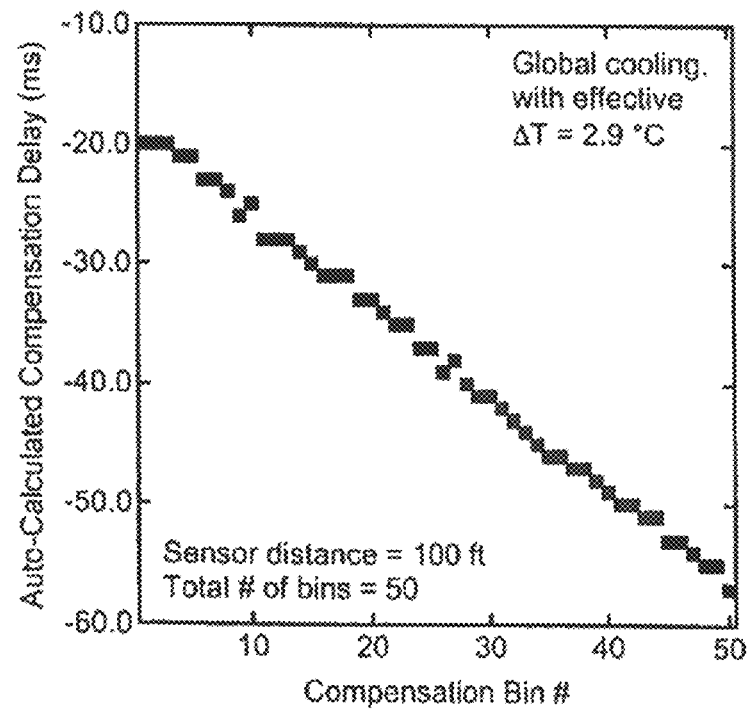

FIG. 13A is a graph of the signal difference amplitude as a function of time for both temperature compensated and non-temperature-compensated signals for a 100 ft. section of a 105-ft long pipe assembly, while FIG. 13B is a graph illustrating the specific delay times that are calculated for each bin (for a total of 50 bins) for the data shown in FIG. 13A.

Figure 14:
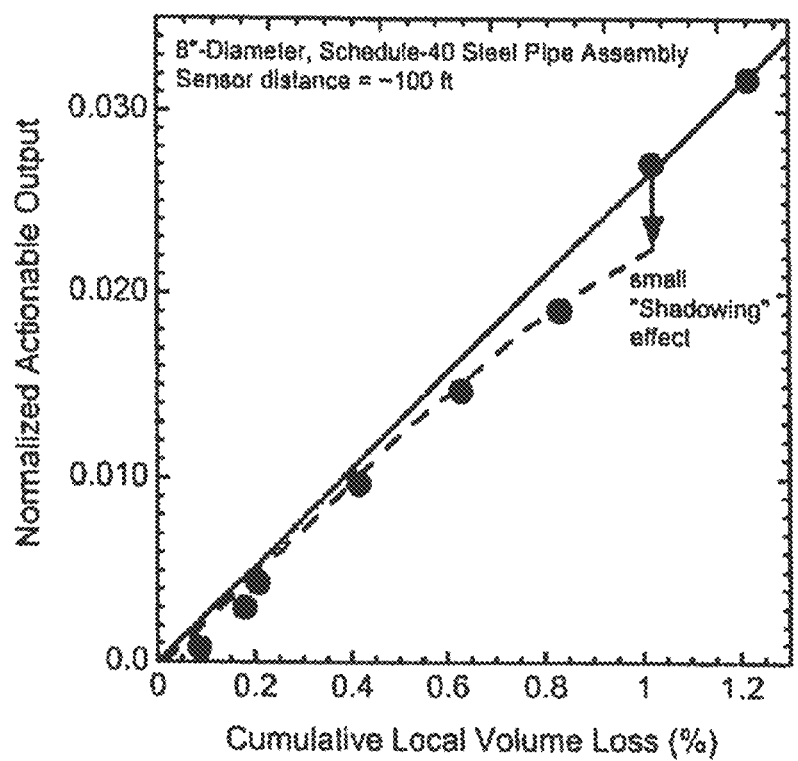

FIG. 14 is a graph of the normalized actionable output calculated by mapping acoustic amplitude, time and frequency data, which may be used as a guide for determining whether action needs to be taken relative to pipe safety, as a function of cumulative local volume loss.

Figure 15A:
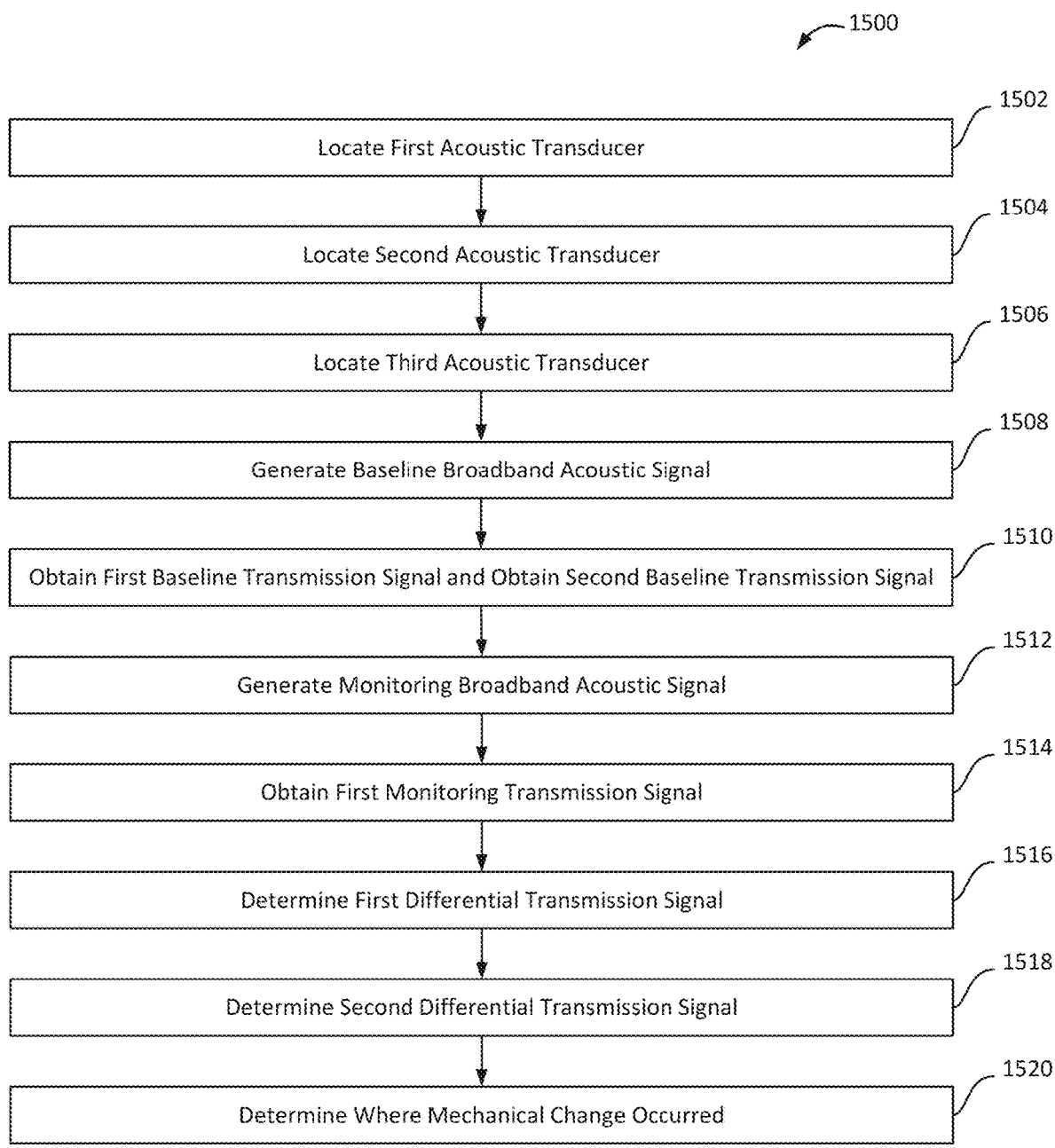

FIG. 15A illustrates a method for detection and monitoring of a mechanical change in an elongated rigid structure, in accordance with one or more implementations.

Figure 15B:
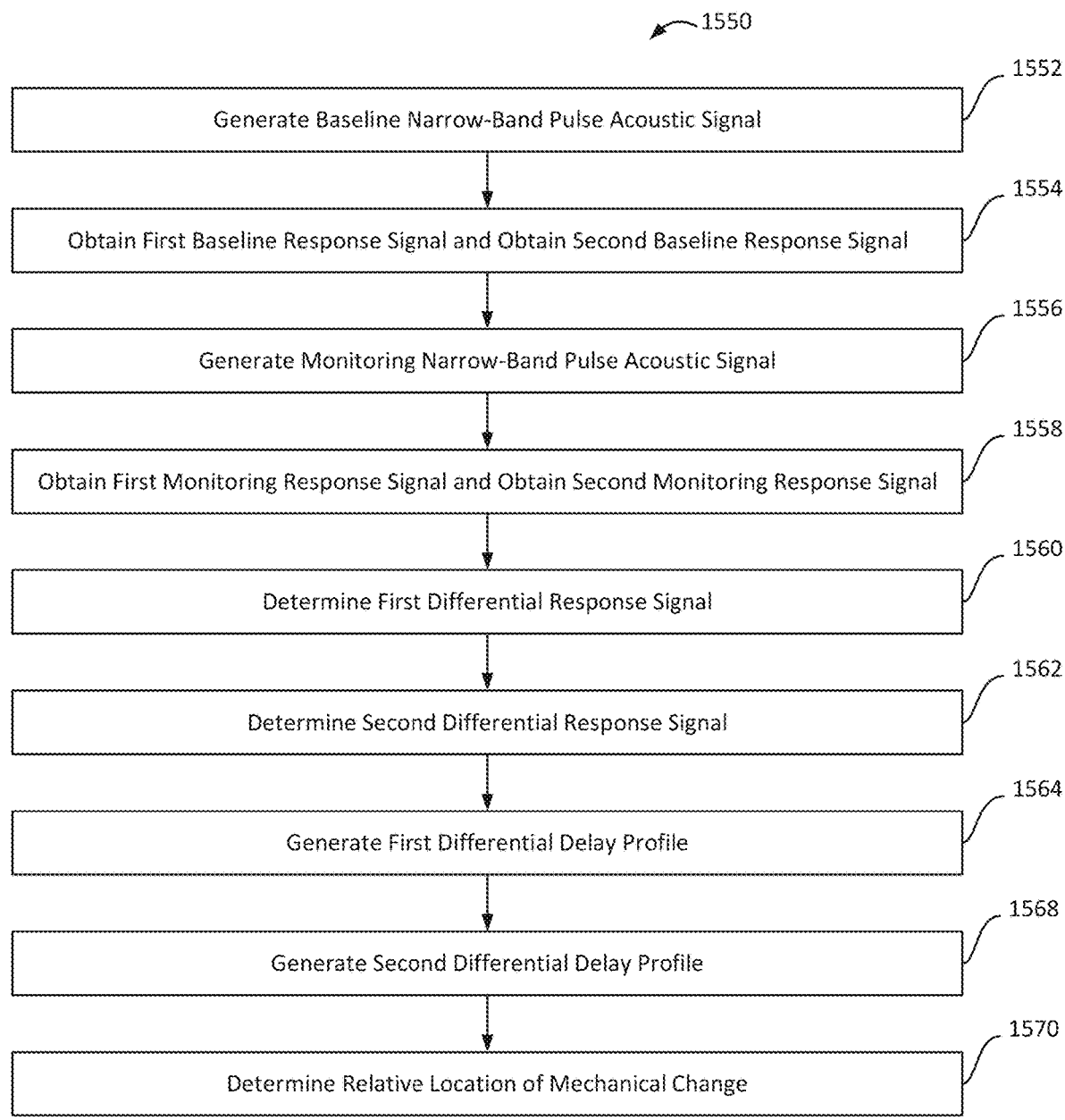
Figure 16A:
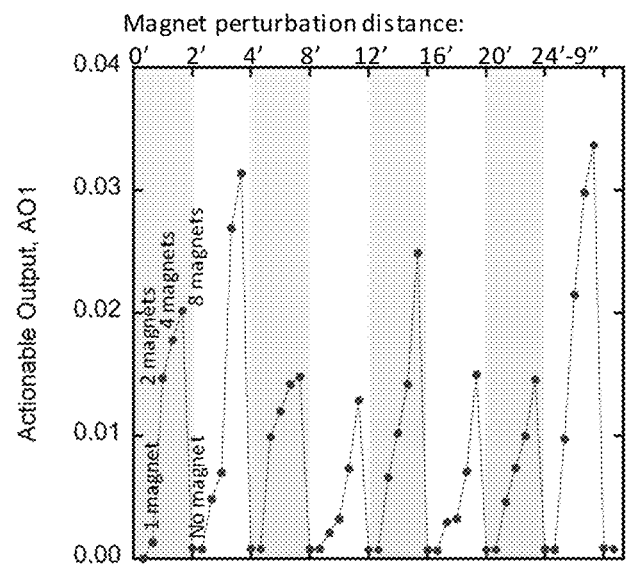

FIG. 15B illustrates a method for detection and monitoring of a mechanical change in a zone of an elongated rigid structure, in accordance with one or more implementations FIG. 16A illustrates a graph of actionable output from a first differential broadband response signal against magnet perturbation distance for an azimuthal distribution of magnets within an elongated rigid structure, in accordance with one or more implementations.

Figure 16B:
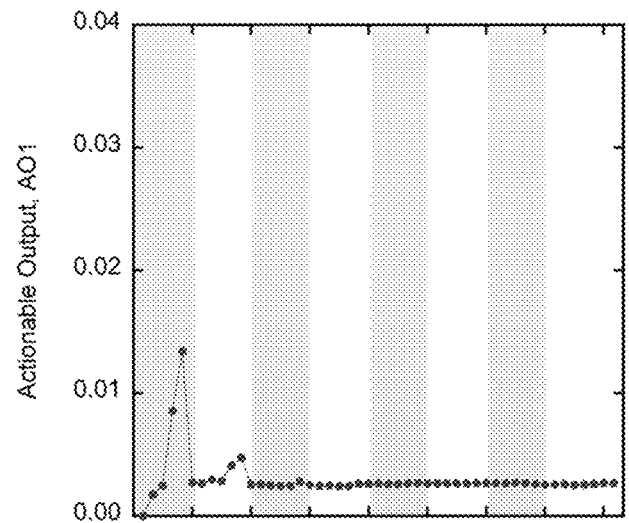

FIG. 16B illustrates a graph of actionable output from a second differential broadband response signal against magnet perturbation distance for an azimuthal distribution of magnets within an elongated rigid structure, in accordance with one or more implementations.

Figure 17A:
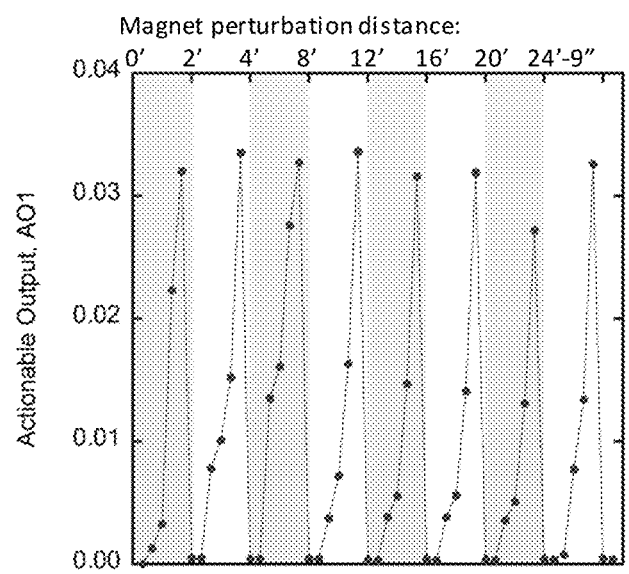

FIG. 17A illustrates a graph of actionable output from a first differential broadband response signal against magnet perturbation distance for an axial distribution of magnets within an elongated rigid structure, in accordance with one or more implementations.

Figure 17B:
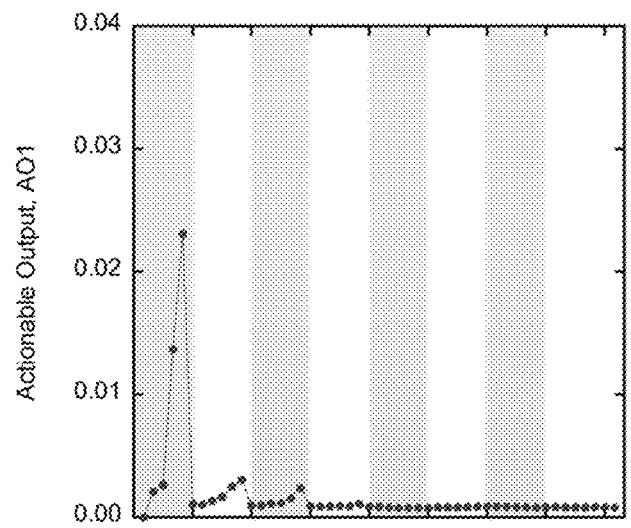

FIG. 17B illustrates a graph of actionable output from a second differential broadband response signal against magnet perturbation distance for an axial distribution of magnets within an elongated rigid structure, in accordance with one or more implementations.

Figure 18A:
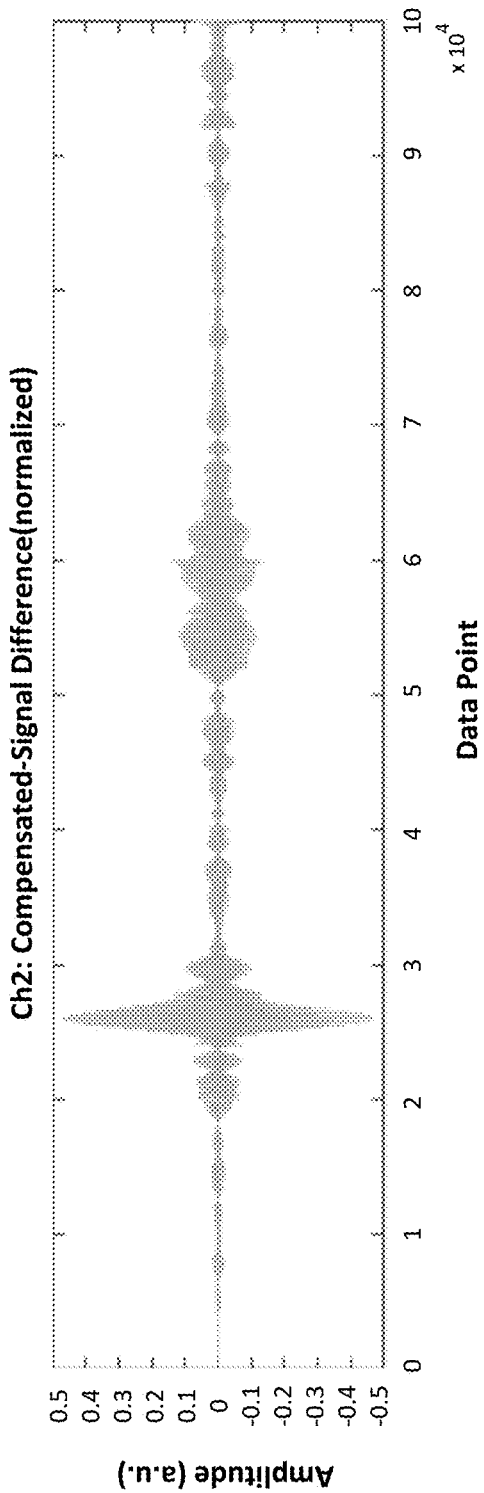

FIG. 18A illustrates a trace of a first differential narrowband response signal for azimuthal distribution of magnets at a given distance, in accordance with one or more implementations.

Figure 18B:
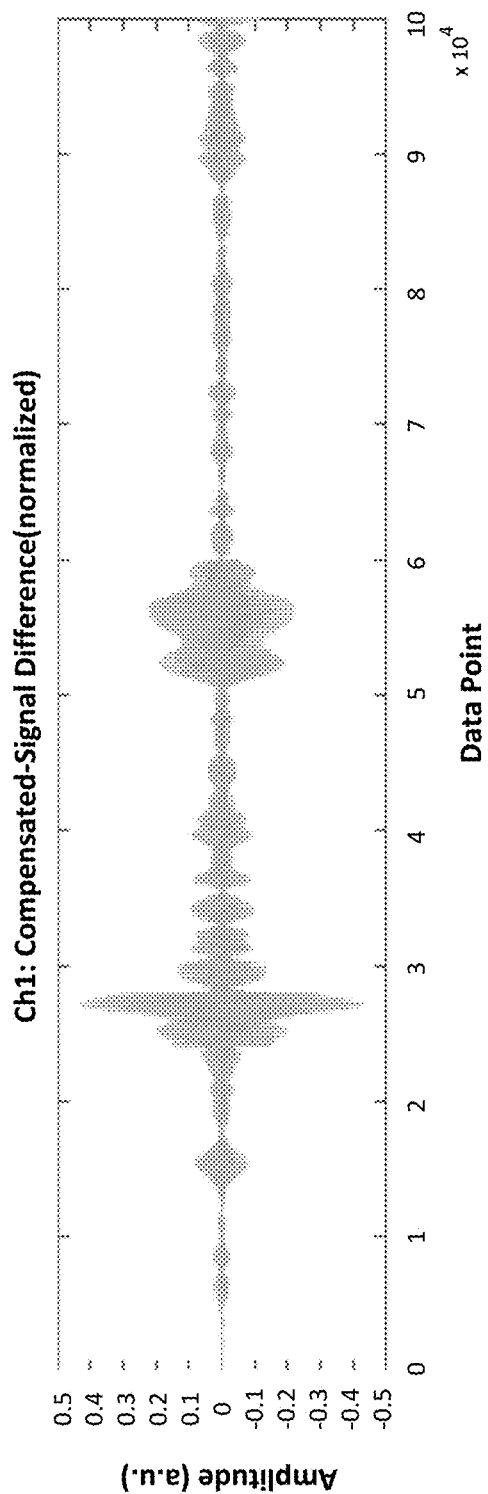

FIG. 18B illustrates a trace of a second differential narrowband response signal for azimuthal distribution of magnets at a given distance, in accordance with one or more implementations.

Figure 19A:
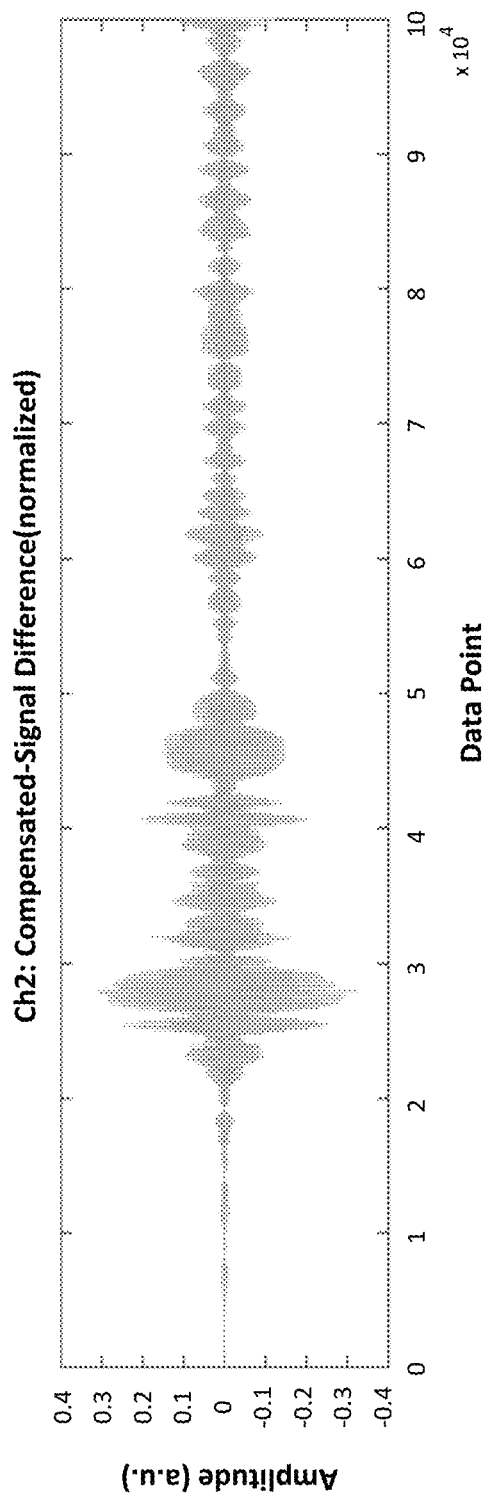

FIG. 19A illustrates a trace of a first differential narrowband response signal for azimuthal distribution of magnets at a given distance, in accordance with one or more implementations.

Figure 19B:
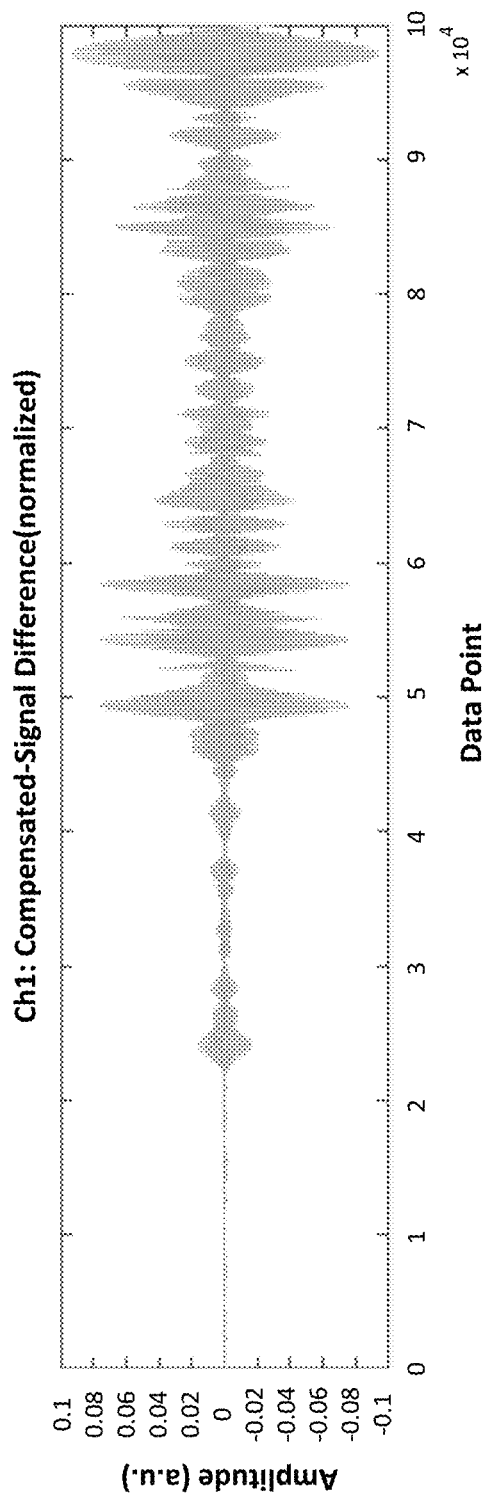

FIG. 19B illustrates a trace of a second differential narrowband response signal for azimuthal distribution of magnets at a given distance, in accordance with one or more implementations.

Figure 20A:
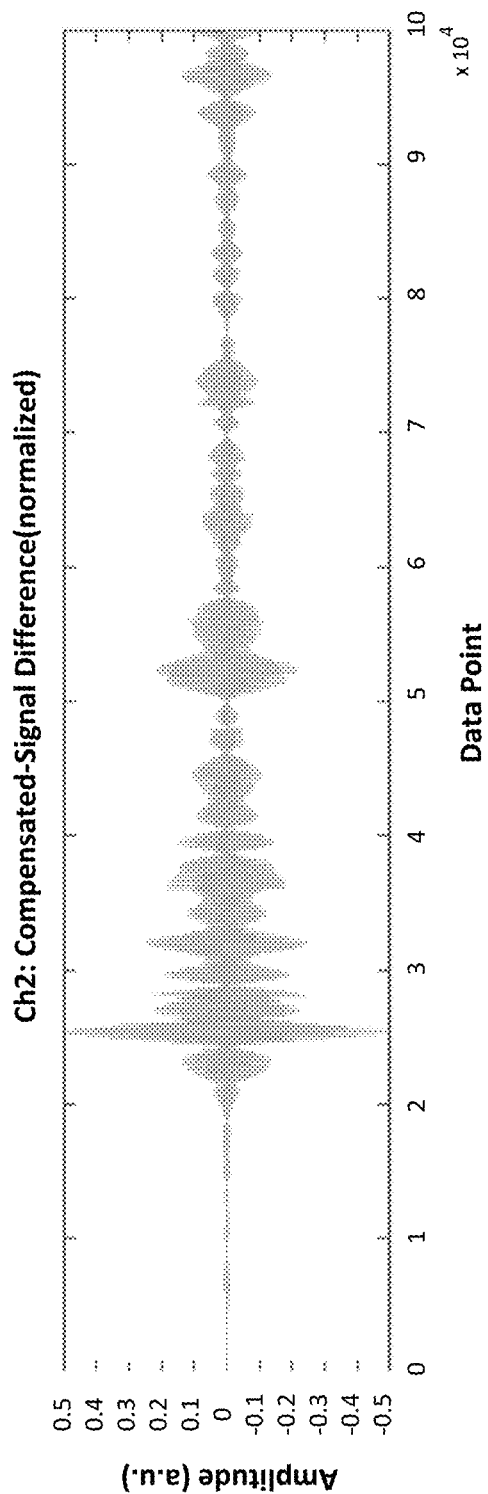

FIG. 20A illustrates a trace of a first differential narrowband response signal for azimuthal distribution of magnets at a given distance, in accordance with one or more implementations.

Figure 20B:
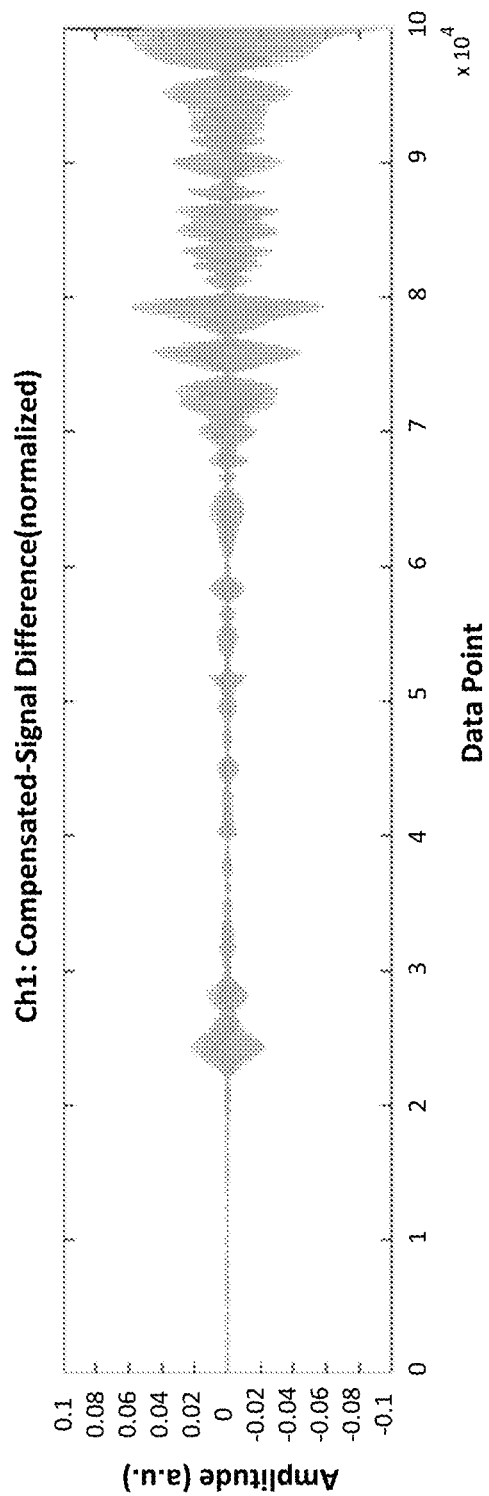

FIG. 20B illustrates a trace of a second differential narrowband response signal for azimuthal distribution of magnets at a given distance, in accordance with one or more implementations.

Figure 21A:
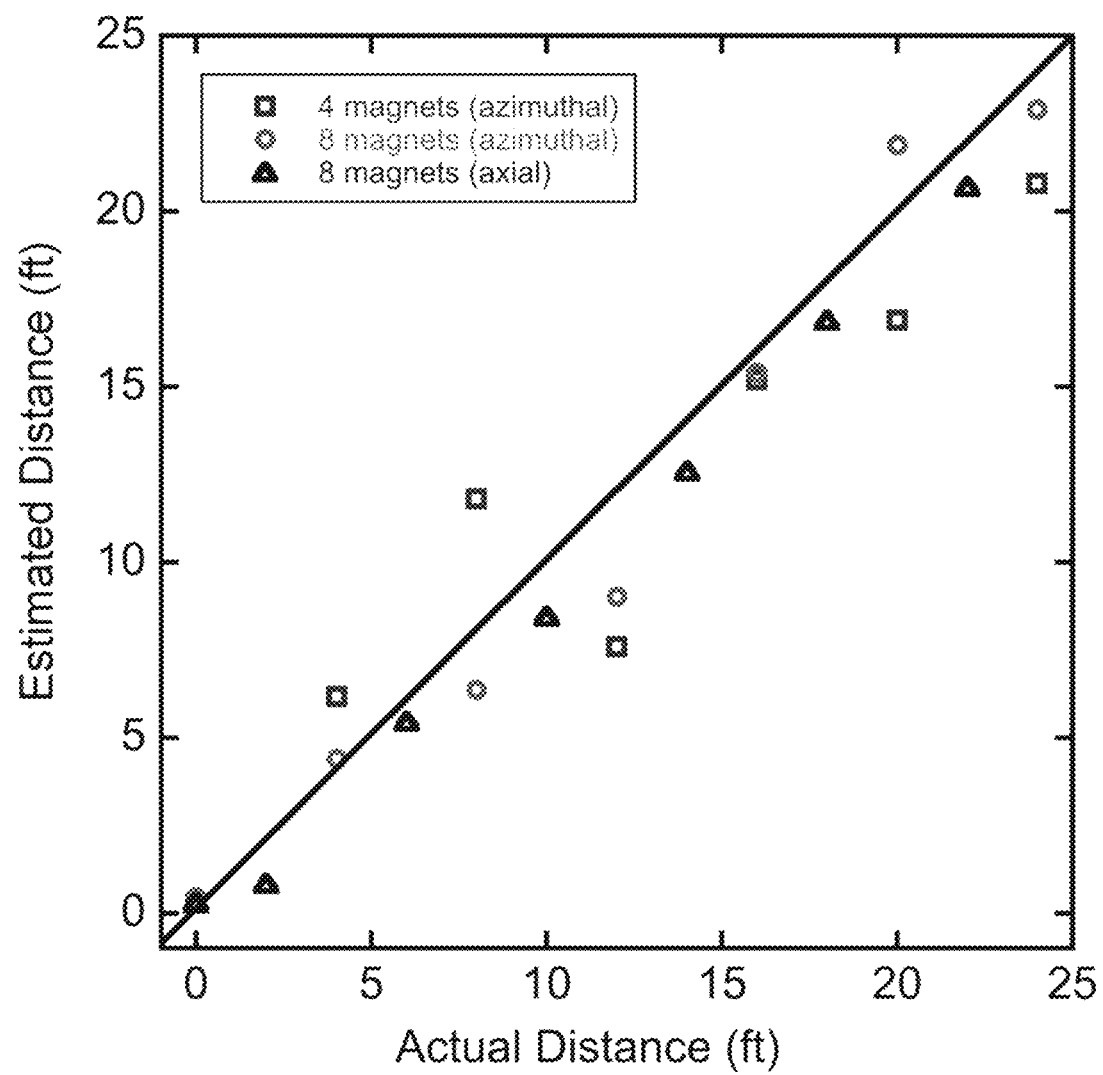

FIG. 21A illustrates a time-domain analysis of differential narrowband response signals, comparing the estimated distance and the actual distance of a defect, in accordance with one or more implementations.

Figure 21B:
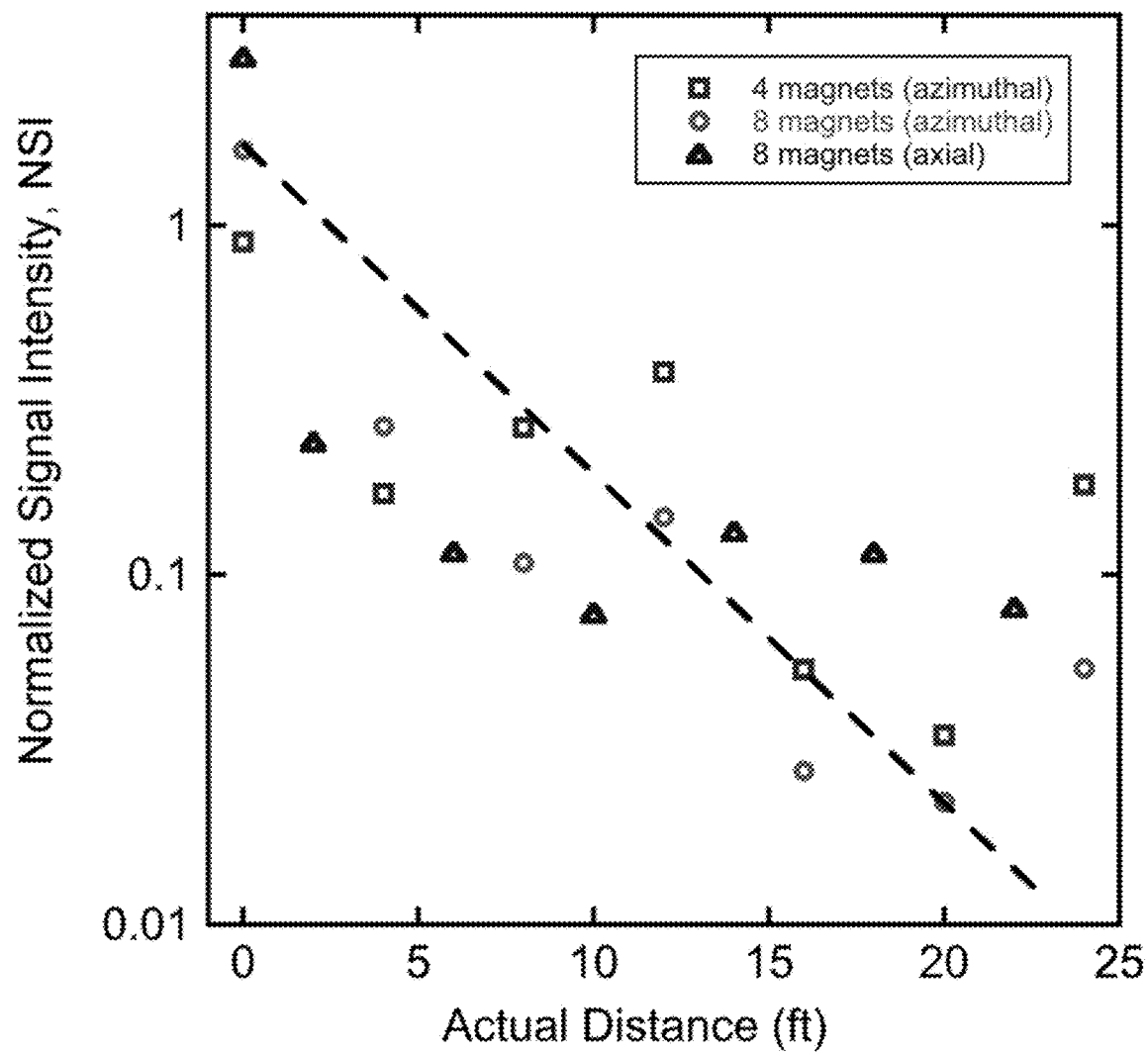

FIG. 21B illustrates a signal-intensity analysis of differential narrowband response signals comparing the normalized signal intensity and the actual distance of a defect, in accordance with one or more implementations.

Figure 21C:
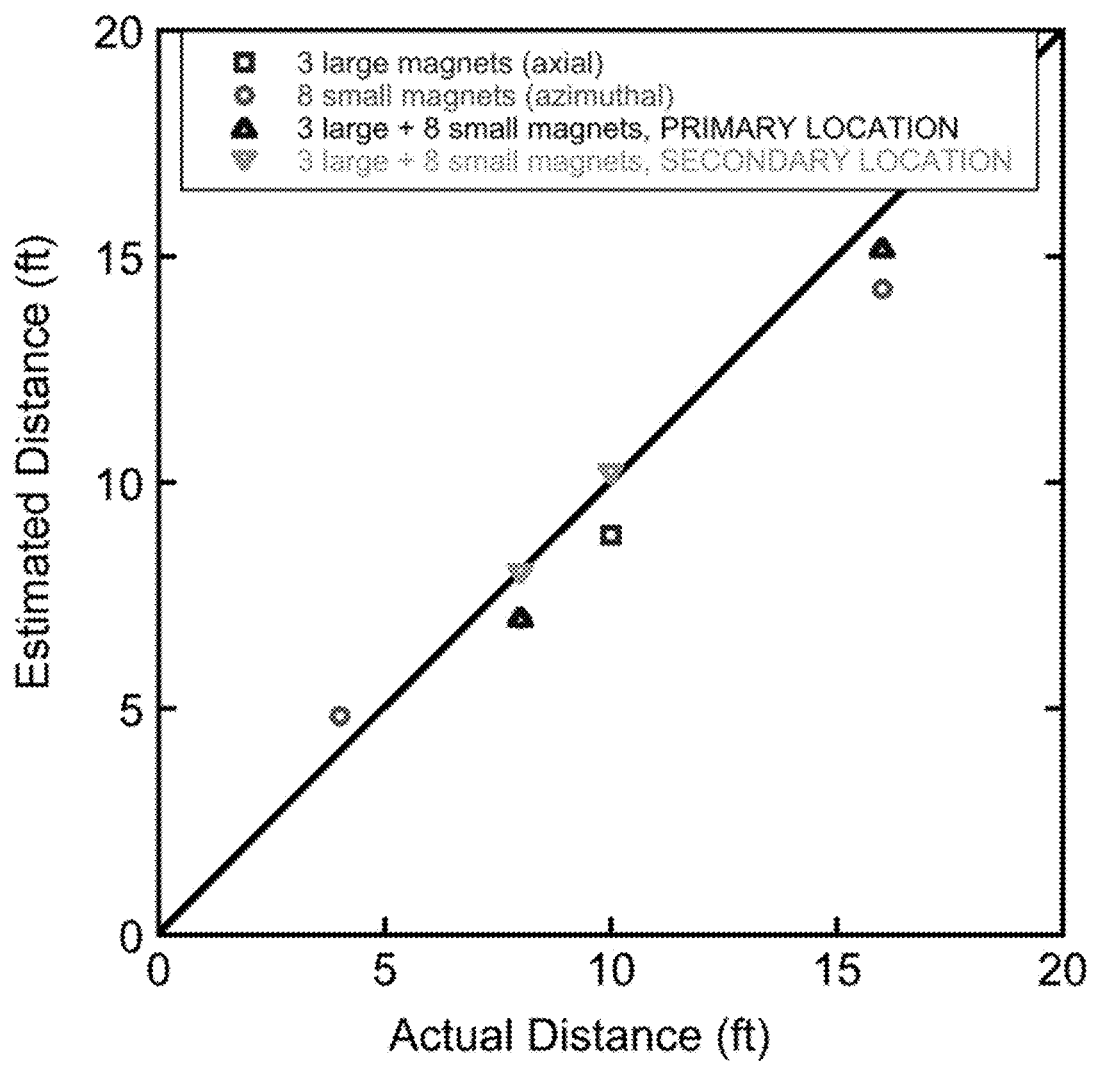

FIG. 21C illustrates a graph of differential narrowband response signals, comparing the estimated distance and the actual distance of one or two defects, in accordance with one or more implementations.

DETAILED DESCRIPTION

Briefly, embodiments of the disclosed technology include methods for acoustic detection and large area monitoring of corrosion and/or erosion, and other defects of metallic structures, such as pipes, vessels, storage tanks, elbows, flanges, reducers, tees, and welds, as examples, in difficult-to-access environments, such as under insulation or under paint. In addition, various pipe geometries and complex pipe geometries involving elbows, flanges, and the like can be monitored.

The present method includes: (i) acoustic signal generation, transmission, and reception with amplitude, time and frequency characteristics that are optimized for the structure/pipe/vessel/tank, and anticipated defect(s); (ii) acoustic data acquisition and numerical analysis of acquired data; and (iii) mapping of amplitude, time and frequency acoustic data characteristics and analysis results into actionable information, for defect identification and defect quantification.

Detectable and identifiable changes in signal energy distribution among the allowed multiple acoustic modes result from the effect of mechanical changes or defects on the propagation of multi-mode acoustic signals through many pipe and vessel segments (or, systems), although the total energy of the acoustic signal is quasi-conserved. That is, defects principally lead to elastic scattering of acoustic waves from one mode to another, while the differential attenuation of total acoustic signal energy is generally small. Mechanical perturbations effective for generating acoustic scattering and attenuation include material loss (pitting, cracks, fractures, and erosion), material conversion (corrosion products), material addition (material migration and accumulation), and material adsorption, each of which having particular scattering/attenuation characteristics in amplitude, time, and frequency phase space.

In accordance with the teachings of embodiments of the disclosed technology, acoustic signals are generated and received at a small number of accessible and convenient locations, such as the ends of pipes, or top and bottom sections of vessels, storage tanks, or elbows, flanges, reducers, tees, or welds, etc. Acoustic signals have amplitude, time and frequency characteristics effective for exciting multiple modes of interest in the pipe, vessel, tank, elbow, flange, reducer, tee, or weld, and such signals propagate in the inspection zone between transmit and receive transducers. Once the structure, pipe, vessel, tank, elbow, flange, reducer, tee, or weld, is characterized in a known or baseline state or condition, such as immediately after installation or after a detailed inspection, the present methods monitor small changes in the transmission characteristics of the acoustic signals in the inspection zone, and identify and quantify the defect formation continually or on-demand, for example, several times per day, once a week, or once a month, over many years by signal differentiation and analysis. The acoustic input and output may be accessed by embedded or mechanically-attached transducers, or by non-contact air coupling, or remote light coupling, as examples.

The acoustic data acquisition may be optimized for high signal-to-noise ratio in the system of interest. Signal analysis combines amplitude, time- and frequency-domain measurements of the signals using Fourier Transforms, Short-Time Fourier Transforms, Wavelet Transforms, Phase Delay Analysis, Hilbert Spectral Analysis, and Hilbert-Huang Transforms, as examples, with the identification and measurement of changes in such multi-dimensional data sets from those of the baseline condition.

The mapping of measured signal characteristics and analysis results for defect identification and quantification allows for interpretation of measured and analyzed data as actionable information.

The received acoustic data are in the form of a transmitted electrical signal amplitude as a function of time, and their acquisition is precisely timed relative to repetitive input excitation in the form of a chirp signal, as an example (using a trigger signal from signal source to receiver instrument), so that one can use time-averaging (usually between 64 and 4096 times). Time-averaging improves signal-to-noise ratio (SNR) and makes the method relatively insensitive to other acoustic (noise) sources in the environment. Filtering the received signal in the frequency domain permits only the spectral components of interest to reach the receiver, thereby further improving SNR.

As an example of signal analysis that could be performed, the time-averaged and filtered received signal is then transformed into a two-dimensional contour/surface map using a Short-Time-Fourier-Transform (STFT) algorithm with optimized parameters of window size, and step size, which may vary depending on the length of the pipe (vessel), and/or characteristics of the pipe or vessel. The STFT map displays the distribution of received signal strength as a function of time and frequency; that is, which frequency components of the transmitted signal arrived, when and with what strength. Joint spectral and time-delay information permits baseline characteristics of the pipe or vessel, as well as the effects of perturbations to the pipe or vessel on the acoustic signal transmission, to be characterized.

The baseline STFT map constitutes the reference level, against which perturbation effects, such as material addition and loss from the pipe wall, water accumulation on pipe walls, material contact with pipe walls, material transformation of pipe walls due to corrosion, strain in pipe walls due to sagging which might be caused by filling of the pipe with liquid, etc., could be analyzed.

Detection sensitivity of embodiments of the present method is the minimum amount of perturbation that can be reproducibly measured; embodiments of the present method have measured perturbation effects due to both material addition and material removal (or, loss) from pipe or vessel walls at levels of <1% local volume change at pipe lengths of up to about 100 ft. Detection selectivity requires distinguishing among the direct causes of acoustic perturbation, such as water accumulation on pipe walls, clamping, sagging, material conversion or loss due to corrosion, material loss due to corrosion pitting, contact of pipe wall with a foreign solid object, etc. For example, water on pipe walls generates relatively uniform attenuation over a wide spectral range of signals, with minimal scattering, and it is therefore readily distinguishable from corrosion pitting and other defects on the pipe which predominantly lead to elastic scattering among specific acoustic modes propagating along the walls of pipes and vessels into other modes with specific time delays.

Paint on the walls (or, chips in the paint) of pipes or vessels have much smaller acoustic perturbation effect than corrosion and other defects. Insulation around the pipes and vessels also produces a weak effect on the acoustic wave transmission compared to corrosion or other defect formation on the pipes and vessels. Clamping a pipe leads to large scattering of acoustic signals and can overwhelm in magnitude scattering effects due to corrosion or other defects. However, the frequency distribution of scattering due to clamping is expected to be much broader than what one would expect from local corrosion scattering, and thus scattering signals can be distinguished. False signals from the effects of clamping may also be avoided by generating a new baseline when a clamp is added or removed from a pipe section.

A foreign solid material locally placed against a pipe is expected to produce acoustic signal scattering similar to those due to material addition to a pipe or vessel wall, and it is expected that it would be difficult to distinguish these effects. Sagging due to weight of a component over time is expected to lead to a spatially diffuse strain field in the pipe. Such a delocalized strain field could lead to weak scattering and attenuation of acoustic waves. However, both the magnitude and the spectral features of such scattering and attenuation should be discernible from scattering due to localized perturbations from corrosion or other defects.

Detection robustness or reliability refers to the long-term viability of the present method, where a baseline can be used to monitor perturbation effects over long time periods, many years in certain applications. To achieve such robustness and reliability, effects of temperature are compensated for, and detrimental environmental noise is filtered. Temperature effects could be present in: acoustic transducer response; coupling coefficient between the transducer and the interrogated medium, such as a pipe; acoustic signal propagation in the medium; and the transfer function of the electronics. The characteristics and relative importance of temperature effects due to each of these components will depend on the specifics of the overall system. However, if the temperature is recorded when initial measurements are made, and subsequent measurements are made within a few degrees Celsius of that temperature, such temperature effects may be too small to alter measurement results. However, if the temperature variation is more than a few degrees Celsius, it may be necessary to employ a method for temperature compensation. Similarly, environmental noise depends on the location where the system resides; thus, noise filtering may be tailored to the specifics of the environment.

As will be described below, a temperature compensation algorithm has been developed and found to increase the signal-to-noise (S/N) ratio, thereby improving measurement sensitivity.

Embodiments of the present method include detection of corrosion in pipes, vessels and structures using acoustic interrogation from a limited number and area of access locations (minimum of two, at two ends of a pipe for excitation and reception of transmitted acoustic signals, the section between the two transducers thereby being monitored). Typically, transmitting and receiving transducers are uniformly distributed over the surface of a pipe about 2 feet to approximately 200 feet apart, with the portion to be monitored therebetween. The pipe section may be straight, curved, flanged, or could have welded portions on it. Pipe sections may be between 2 ft and 200 ft in most cases, and the present method is similarly applicable to situations where cross-sectional dimensions of the pipe are much smaller than the length of the pipe. Large flanges, T-sections, or 4-way or 6-way crosses attached to a pipe may be monitored separately.

Figure 1A:
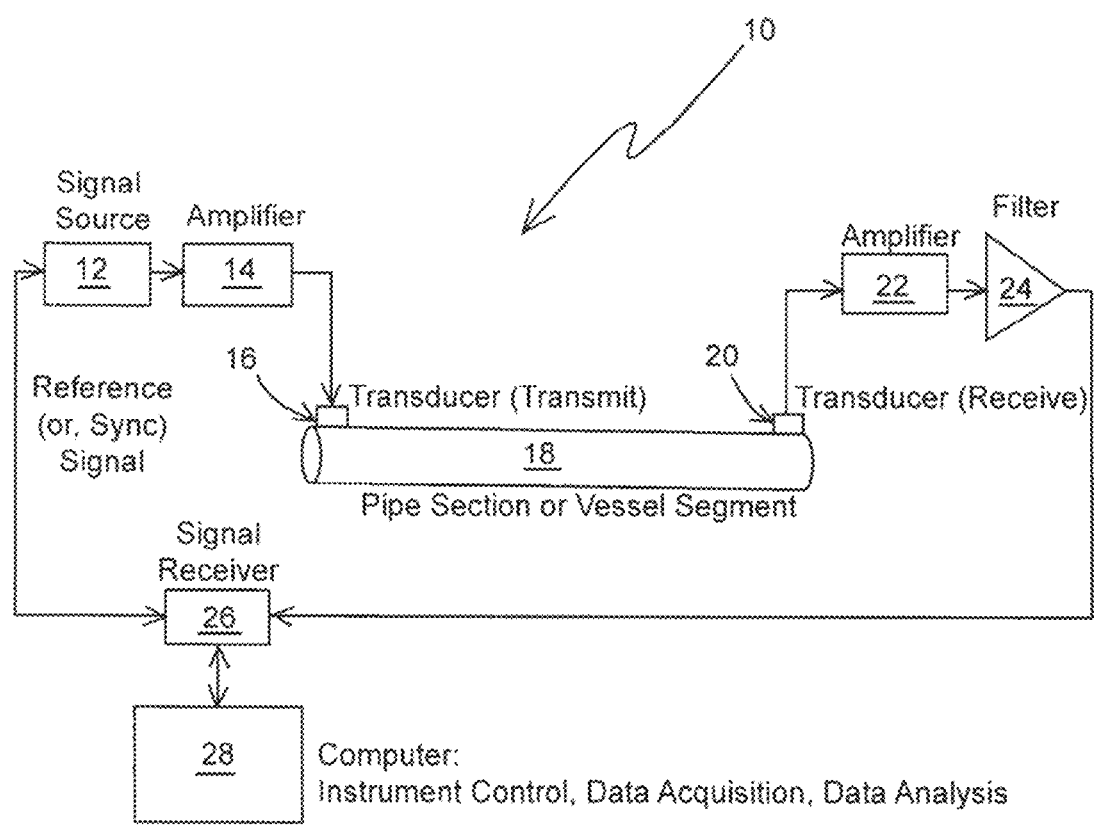

Reference will now be made in detail to the present embodiments of the disclosed technology, examples of which are illustrated in the accompanying drawings. In the figures, similar structure will be identified using identical reference characters. It will be understood that the figures are for the purpose of describing particular embodiments of the disclosed technology and are not intended to limit the invention thereto. Turning now to FIG. 1A, a schematic representation of an apparatus, 10, for practicing embodiments of the method of the disclosed technology is shown. Signal source, 12, provides a chosen ultrasonic signal, amplified by amplifier, 14, to one or more transmitting transducers, 16, shown mounted at one end of a linear pipe section or vessel segment, 18. Acoustic signals having propagated through pipe or vessel section 18 are detected by receiving transducer, 20, disposed at the opposite end of the pipe or vessel section 18 from transmitting transducer 16. The electrical signal generated by receiving transducer 20 is amplified by amplifier, 22, and filtered by filter, 24, before being directed to signal receiver, 26, is synchronized (triggered with a specific time delay with respect to) with signal source 12. These signals are processed by signal receiver 26, and the processed signal is directed to computer, 28, for data acquisition and analysis. Computer 28 also controls elements 12, 14, 22, 24, and 26.

Separate pre-amplifier and filter modules may be used for each transducer, all electronic components being wired together using coaxial cables or USB cables. In this configuration, re-connection of the wires is required for using any transducer as transmit or receive sensor, although all transducers are identical and can serve as transmit or receive sensors without any modification. A network of sensors and communication apparatus, all wirelessly connected to a central computer for instrument control, data acquisition, and data analysis, may be used to accommodate multiple transducers. Each sensor would have a unique RFID tag, and an integrated electronics module for both transmit and receive functionality. Such dual functionality would make the system readily re-configurable, and enhance the robustness against defective or failed sensor components. Power for the sensors and integrated modules may be provided by batteries, and charging energy might be harvested from solar power or environmental vibrations, as examples.

Vessels may be monitored in segments, where each segment has relatively uniform wall thickness and physical proximity. If the vessel segments have significant non-uniformities, such as welded ribs or other physical attachments, then (more than one) transmit transducer and (more than one) receive transducer may be used. The number of transmit and receive transducers will be commensurate with the non-uniformity of the segment, and the areal size of the segment. Increasing the number of transmit transducers will permit more uniform acoustic excitation, and sampling of "all" parts of the segment will lead to better sensitivity, selectivity, and robustness of detection of corrosion and other defects. Additionally, the increased number of receive transducers will introduce redundancy to the system, which will make the present method more reliable and robust.

Figure 1B:
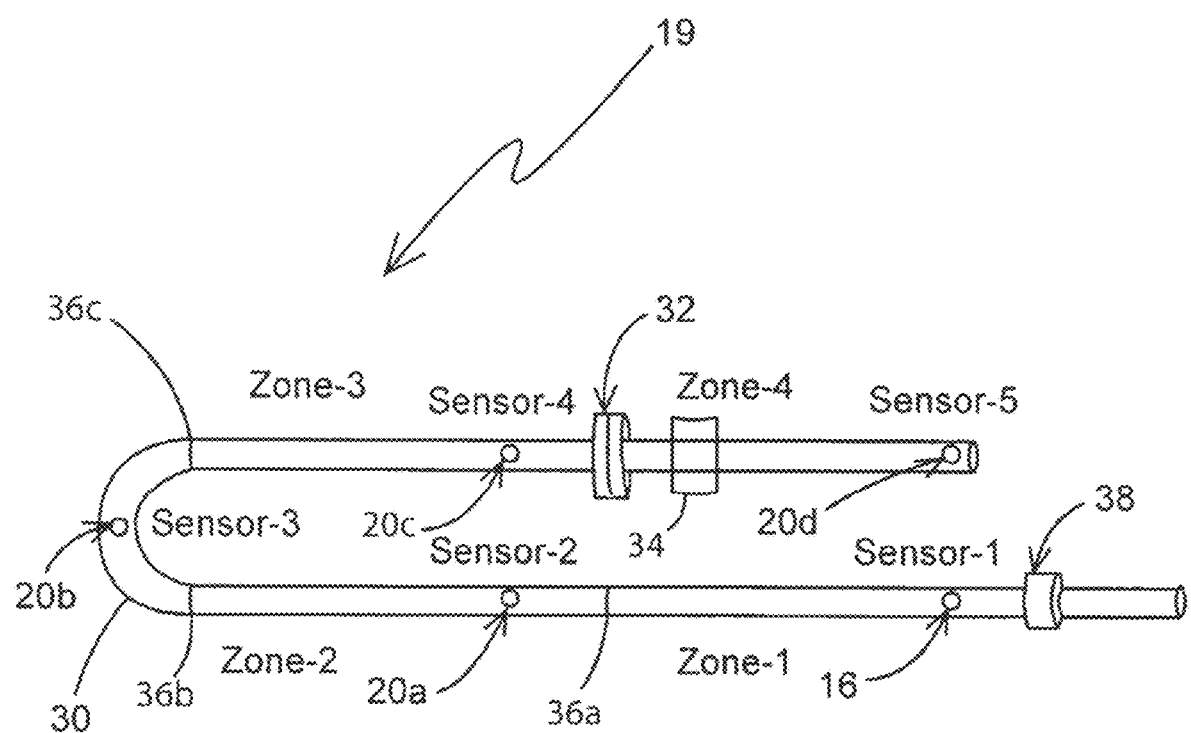
FIG. 1B is a schematic representation of a more complex pipe configuration, for which the present apparatus may be employed.

FIG. 1B is a schematic representation of a pipe assembly having a more complex series of attached pipe sections, 19, (105-ft-long, 8-in-diameter schedule-40 carbon steel pipe with two 90°-elbows, 8 welded-joints, and 1 pair of flanges, the assembly supported by 10 stands.) that may be monitored in accordance with embodiments of the disclosed technology. Five, evenly spaced (approximately 25 ft. apart) transducers 16, 20a, 20b, 20c, and 20d, are permanently-attached along an about 100-ft section of the pipe, having curved section, 30 (two 90°-elbows). Although only one transducer 16 is identified as a transmitting transducer (FIG. 1A), all five transducers may both transmit and receive. Zones marked 1 through 4 define minimum interrogation areas of the pipe (about 25 ft. in length) using the apparatus illustrated in FIG. 1A, when nearest sensors are used for transmit and receive. For example, Zone-4 is an approximately 25 ft. section of the pipe assembly between Sensor-4, 20c, and Sensor-5, 20d, and includes flange connection, 32, and material removal area, 34. Larger lengths areas may be interrogated by using further-separated sensors. For example, all four zones may be interrogated at the same time by using Sensor-1, 16, as the excitation (transmit) sensor and Sensor-5, 20d, as the receive sensor. Three welded sections, 36a-36c, are also illustrated, as is commercial sensor array collar, 38.

As stated above, each attached transducer may function both as a transmit and a receive transducer, thus eliminating the need to attach extra transducers in certain neighboring pipe sections or vessel segments when a network of interconnected pipes and vessel segments are to be monitored.

Using multiple sensors along the length of a piping section to monitor that piping segment can lead to additional localization information of where the changes occurred. It is possible to provide some estimate the location of dominant wall loss in a zone by monitoring the amplitude of signal in adjacent zone. Specifically, the amplitude of signal in the adjacent zone decreases as a function of the distance of dominant wall loss from the shared transmitting transducer. Another adjacent effect that could be utilized to estimate the location of dominant wall loss is related to the time of arrival of dominant scattered signals. The delay time of the dominant scattered signal from the neighboring zone is related to the distance of the dominant wall loss area from the transmitting transducer and receive transducer on the other end of the adjacent zone.

Figure 1C:
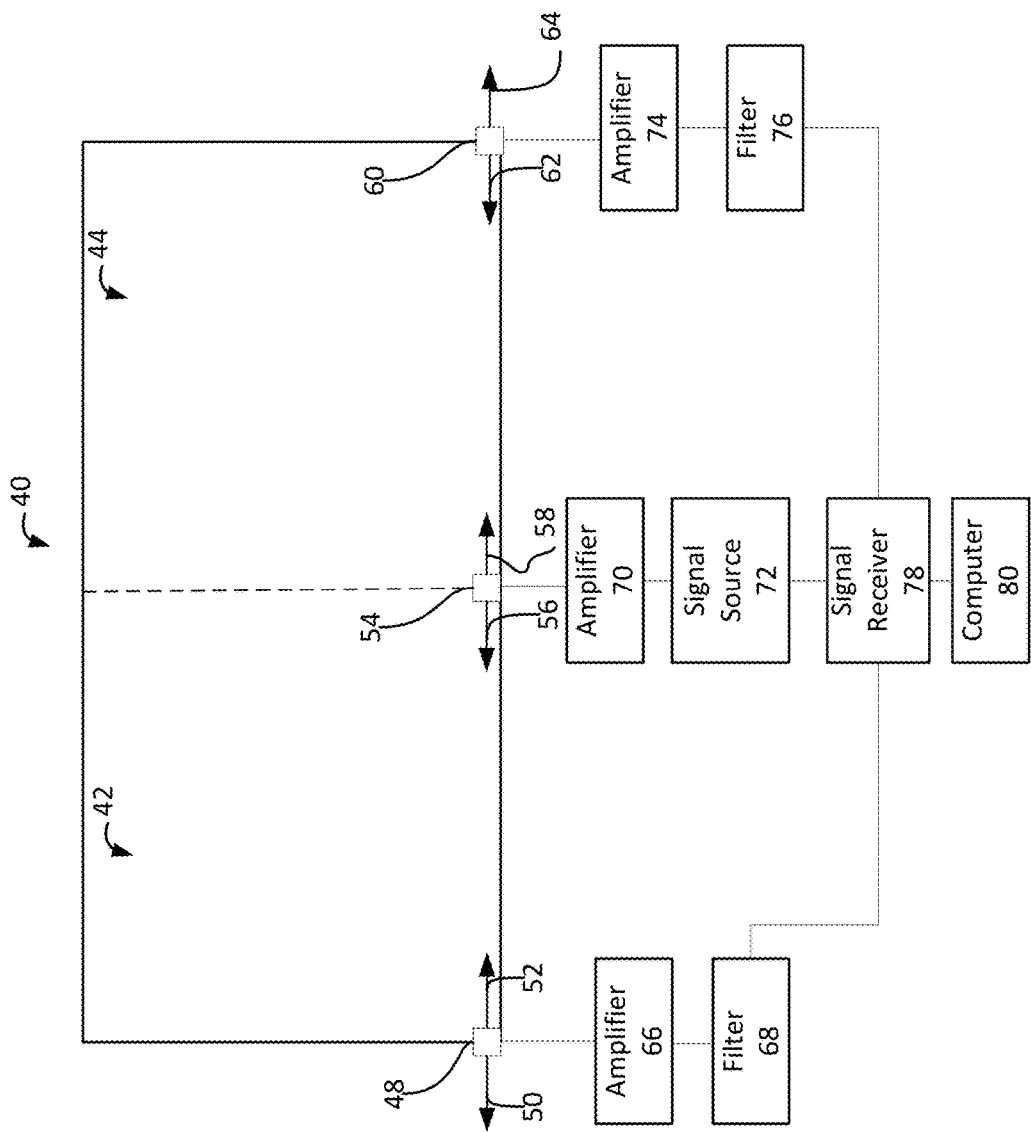
FIG. 1C illustrates a representation of an example rigid structure where acoustic signals may be sent and received, in accordance with one or more implementations.

FIG. 1C illustrates a representation of an example rigid structure where acoustic signals may be sent and received, in accordance with one or more implementations. Rigid structure 40 may include two zones 42 and 44. Rigid structure 40 may include transducers 48, 54, and 60. Transducers 48, 54, and 60 may generate acoustic signals 50 and 52, 56 and 58, and 62 and 64 respectively. Signals 50, 52, 56, 58, 62, and 64 may be broadband, narrowband, and/or other types of signals. Signals 50, 52, 56, 58, 62, and 64 may include pulse echoes, such that multiple signals are sent around the same time. Sending relatively concurrent signals may help identify what part of zone 42 and/or 44 has a defect. Signals 50, 52, 56, 58, 62, and 64 may be a single-tone Gaussian-enveloped pulse to help determine delay differences in signals 50, 52, 56, 58, 62, and 64. FIG. 1C may operate similarly to FIG. 1A.

Transducer 48 may receive, or obtain, signal 56 from transducer 54.

In one example, a method for locating an anomalous feature on a rigid structure may include selecting a frequency chirp signal having a signal strength between about 1 and about 100 V. The method may include selecting a spectral content of between about 10 kHz and about 200 kHz. There may be several longitudinal, torsional, and flexural modes (L-, T-, and F-modes, respectively) that support acoustic signal propagation at kHz-MHz frequencies in pipes and vessels having wall thicknesses ranging between ⅛ in. and 4 in. Therefore, between about 1 kHz to about 1 MHz is effective for acoustic interrogation of corrosion and other defects, because such acoustic modes are sensitive to various defects and mechanical perturbations. A duration between about 0.1 ms and about 10 ms, and a repetition rate between approximately 10 ms and approximately 1000 ms, are useful for the interrogating excitation signal;

In some examples, a time-average of between about 64 and about 4096 repetitions may be used. In some examples, a filter, such as a band-pass, and/or low-pass, and/or high-pass filter, may be used to filter the signal. In some examples, the filter may remove the DC component from the first received signal so that only AC components remain. The method may also include normalizing the signal strength of the first received signal and the second received signal so that the strongest component in either signal equals a chosen number. The method may include performing STFT of the time-averaged, first and second AC received signals with chosen time and frequency window sizes, and time steps, (for example, a Hamming Window size of 1024, and a step size of 32 with a frequency increment of 1 kHz and a time increment of 100 ns were used for 20-ft-long, 2¾ in.-diameter (¼ in.-wall-thickness) pipe).

In some examples, the method may include taking the difference between normalized first and second STFT 2D surface/contour maps obtained in a similar manner to that of the baseline or reference STFT at a chosen time, T, when a perturbation is expected, or during routine testing and the baseline or reference ND-STFT at T=0, forming a new STFT 2D surface/contour map, which illustrates energy loss and energy gain among acoustic modes.

In some examples, the method may include identifying specific frequency-time mode pair(s) in the 2D map where scattering event(s) (or set(s) of events) can be discerned (a scattering event will appear as a bump, or crest (positive signal), with a corresponding dip or trough (negative signal), in the ND-STFT map.).

In some embodiments, the method may include generating the amplitude difference between crest of the feature having the maximum height and the trough of the corresponding feature having the minimum depth in the ND-STFT map (that is, the maximum signal difference). The method may also include using the maximum signal difference (or, ND-STFT Signal Range) calculated in accordance with step 8 in the embodiment of the method described hereinabove, is one way of mapping the 2-Dimensional data into a scalar. As will be described in the EXAMPLES, this approach has been successfully used to quantify the level of corrosion or defect in a pipe section or vessel segment, and has been found to yield a monotonic, near-linear relationship between the level of mechanical perturbation (material loss or material addition) and ND-STFT Signal Range for pipes and vessels.

As stated above, ultrasonic waves may penetrate through the thickness of structural elements and can travel long-distances, allowing interrogation of large areas all at once by using a small number of spatially-distributed ultrasonic sensors, with damage being detected by baseline subtraction. When environmental and operational conditions change, the propagating medium and ultrasonic wave behavior also changes, limiting the effectiveness of baseline comparison in distinguishing damage from environmental and operational effects. A ubiquitous environmental effect is temperature change. Many methods have been developed and implemented to compensate for temperature in structural monitoring applications, with varying effectiveness under different conditions. In accordance with the teachings of embodiments of the present methods effective temperature compensation is provided for a broad set of tested conditions: 1) ultrasonic excitation with multiple modes, or hybridized modes, in specular and diffuse regimes; 2) ultrasonic propagation in homogeneous and non-homogenous media involving multiple reflections, and broad spectral and wide temporal range signals; and 3) autonomous compensation with a wide range of global and local temperature fluctuations in the interrogated medium without the need to know the actual global or local temperatures.

Existing temperature compensation methods, such as optimal signal stretch (OSS) method, estimate a stretch factor through multiple iterations of all expected outcomes, which is computationally inefficient. Moreover, these methods are best suited for simple geometries having pure time-stretch effects, whereas the embodiments of the present method are applicable to more complex geometries having time-stretch as well as signal distortion effects.

Embodiments of the present method for temperature compensation are effective for: single as well as multiple and hybridized modes; homogeneous and inhomogeneous media, with a wide range of reflective components; and in the presence of both global and local temperature variations.

No single time-stretch factor is sufficient to adequately compensate for temperature effects in a real-world monitoring system, where there will be local and global temperature variations, and realistic structures will have varying degrees of inhomogeneities (leading to corresponding varying amounts of reflections), and will support a variety of modes for ultrasonic wave propagation with varying temperature effects. Thus, the present method generates an appropriate set of time-delay factors to replace the single time-stretch factor that is commonly used in other temperature compensation methods.

When ultrasonic signals arrive at the receiving sensor, they accumulate all the phase shifts that they encounter in the pipe, and all the modes and reflections, thus phase-shifted, combine to form a complex waveform. This waveform is distributed in time. As will be described below, this time-distributed waveform is divided into bins, each bin of a waveform segment being temperature compensated using a single delay factor. The delay factor for each bin is calculated using cross-correlation between the real-time measured data and the previously measured baseline data, without any direct knowledge of local or global change of temperature in the interrogated medium. The time delay for each bin is the peak position of the cross correlation function. Once each bin is temperature compensated, the bins are combined to form a temperature-compensated waveform.

The minimum size of the bins is determined by the minimum wavelength of the ultrasonic waves of interest, and the maximum size of the bins is determined by the time delay dependence of the phase shift that is to be compensated. In practice, bin sizes are empirically or theoretically optimized; it is usually between approximately 0.01 ms and about 1 ms, for adequate temperature compensation in a practical monitoring system. The number of bins also depends on the specifics of the monitoring system. In practice, it may vary between about 10 and about 1000.

Embodiments of the present disclosure may provide sensitive and selective diagnostics for pipes and vessels for changes including:
1. Water accumulation on pipe/vessel walls, which could be a precursor to corrosion;
2. Significant paint chipping or major insulation degradation, which again could be a precursor to corrosion;
3. Excessive pipe sagging, which could lead to microcracking and other mechanical degradations;
4. Solid object leaning strongly against a pipe or vessel wall, which could lead to localized degradation of pipe integrity; and
5. Internal clogging of pipe walls or blockage of pipe, which could lead to flow problems and/or internal corrosion, etc.

Volume changes of less than 0.1% in pipe wall sections of 50-ft-long pipe may be detected.

Having generally described the disclosed technology, the following EXAMPLES provide additional details. EXAMPLES 1-4 describe ND-STFT method (1).

Example 1

The effect of material addition through attachment of small magnets on pipe walls is demonstrated:

FIG. 2 shows the received signal after 20-ft transmission along an empty corroded pipe having 10" diameter, and approximately ½" wall thickness, and used as a baseline. The transmitted linear chirp, was 10 V peak-to-peak, between 5 kHz and 200 kHz, with 1 ms duration, and repeated every 100 ms. FIG. 3 shows the same received signal after 20-ft transmission along the empty corroded pipe with 10" diameter, and ½" wall thickness mentioned in FIG. 2, hereof, but perturbed by attaching, 12 small magnets on the pipe wall generating a local volume change of about 3% on the pipe wall. The two normalized signals show, at first impression, little difference in the time/frequency domain.

FIGS. 4A-4C are graphs of the ND-STFT signal calculated by taking the difference between the first (baseline) and the second (perturbed) signal intensities shown in FIGS. 2 and 3 discussed hereinabove, for 2, 4 and 12 attached magnets, respectively, while FIG. 5 is a graph of the difference of the maximum height and the minimum depth in the ND-STFT map (that is, the maximum signal difference), as a function of magnets attached.

Example 2

The effect of material removal through drilling of pockets on pipe walls for an uncorroded pipe having 20'-length, 2¾"-dia, W-wall thickness:

FIG. 6 is a graph of the difference in the maximum height and the minimum depth in the ND-STFT map (that is, the maximum signal difference), or, equivalently, the STFT difference signal intensity, as a function of material removed (or, pit volume ratio).

Example 3

The effect of material removal through grinding holes on vessel walls (in this case vessel segment is the entire vessel), wherein 4 transmitting transducers and 1 receiving transducer were employed:

FIG. 7 is a graph of the received signal with no perturbation (baseline), while FIGS. 8A-8C are graphs of the ND-STFT signal (difference between the baseline and after 0.2 cc, 0.6 cc and 1.2 cc of material, respectively, was removed by grinding.

FIG. 9 is a graph of the difference between the maximum height and the minimum depth of the ND-STFT map (that is, the maximum signal difference), as a function of removed material for an empty vessel.

Example 4

The effect of material addition through attachment of magnets on vessel walls (in this case vessel segment is the entire vessel, wherein 4 transmitting transducers, and 1 receiving transducer were employed:

FIG. 10 is a graph of the difference between the maximum height and the minimum depth of the ND-STFT map (that is, the maximum signal difference), as a function of added material (magnets) for an empty vessel.

EXAMPLE 5 illustrates the use of temperature-compensated ND-STFT method (3).

Example 5

Examples of temperature compensation are given below for experiments conducted on the approximately 105-ft-long pipe assembly. In FIGS. 11 A, 11B, 12A, 12B, 13A, and 13B, the 25-ft sensor distance is for transducers 20*a*, performing as a transmitter and 20*b*, performing as a receiving transducer; the 50-ft sensor distance is for transducers 20*b*, performing as a transmitter and transducer 20*d*, performing as a receiver; and the 105-ft sensor distance is for transducers 16 and 20*d*.

FIG. 11A is a graph of the signal difference amplitude as a function of time for both temperature compensated and non-temperature-compensated signals in a situation where there has been no material loss, conversion, or addition between the measurements. The non-temperature-compensated signal difference is calculated by subtracting a reference (baseline) signal from a subsequent measurement signal in the time-domain, whereas compensated signal difference is calculated by subtracting reference signal from a temperature-compensated subsequent measurement signal, as described above. As may be observed, in the FIG. 11 A, the amplitude of the difference signal is reduced significantly after temperature compensation; that is, the spurious signal due to temperature variation is significantly reduced. Thus, temperature compensation reduces the spurious signal level, thereby resulting in an improved sensitivity limit for detection of material gain or loss.

FIG. 11B is a graph illustrating the specific delay times that are calculated for each bin (for a total of 25 bins) for the data shown in FIG. 11A. As mentioned above, these delay times are used to shift the time-domain waveforms in each bin, and the temperature-compensated signal is generated from a combination of such compensated waveforms from each bin. FIGS. 11A and 11B therefore show the effect of temperature compensation on the signals, and the specific delays that were calculated for each bin to achieve this result.

FIGS. 12A and 12B are graphs illustrating the same results for a 50 ft. transducer distance, using 25 bins, and FIGS. 13A and 13B are graphs illustrating the same results for a 100 ft. transducer distance using 50 bins, respectively. The slopes for FIGS. 11B and 12B are positive because the temperature variation is positive, whereas that for FIG. 13B is negative because the temperature variation is negative.

Effectiveness of temperature compensation may be quantified by using sensitivity improvement factor (SIF) which is defined as the ratio of spurious difference signal strength without compensation to difference spurious signal strength with compensation. In some examples, the method may include selecting a frequency chirp signal having selected parameters. For example, the frequency chirp may have a signal strength between about 1 V and about 100 V. Example frequency chirps may include spectral content of between about 10 kHz and about 200 kHz. In some embodiments, the spectral chirp may have a duration between about 0.1 ms and about 10 ms. Example frequency chirps may have a repetition rate between about 10 ms and about 1000 ms.

Embodiments may include calculating a time-average (e.g., of between about 64 and about 4096 repetitions) and filtering the received signal. For example, filtering may include applying a band-pass, a low-pass, a high-pass, or other filters as known in the art. The received signal may be a reference or baseline signal.

Experiments may show that the disclosed method may compensate for temperature effects when: different modes are present, the medium is not homogeneous, there are significant scattered waves, and there are local as well as global temperature changes, while having little spurious effect on waveform changes due to simulated or real damage.

FIG. 14 is a graph of the normalized actionable output (scalars) as a function of cumulative local volume loss for the 105-ft-long pipe assembly described in FIG. 1B hereof, for sensor-to-sensor distance of 100 ft. The volume loss on the pipe wall was simulated by removing material from the pipe wall with a grinder. Between 0.1 and 0.8% local volume loss the material was removed along the axis of the pipe in the shape of square pockets, with small shadowing effect. The data for 1% and 1.2% were obtained when material was removed circumferentially with respect to last square pocket. In this case, no significant shadowing effect is observed. These results show that embodiments of the present method are applicable for long distances in the presence of significant non-uniformities (flanges, elbows, bends, stand connections, etc.), and are linear over a wide range (0.1 to 1% local volume loss). The sensitivity limit, which is about 0.1% volume loss in this example, is determined by the effect of operational environment on the temperature variation and the effectiveness of the present temperature method. This sensitivity limit of 0.1% local volume loss is preserved for environmental temperature fluctuations of ±3° C. For a temperature variation of ±10° C., this sensitivity limit expands to about 0.5%.

EXAMPLE 6 illustrates the use of broadband, multi-mode, transmission-reflection, scattering technique with distributed single sensors.

Example 6

Examples of acoustic large area monitoring are provided for experiments conducted on an approximately 50-ft-long pipe assembly using magnets that were about ½ inch by about ½ inch by about ⅛ inch. In the example, source transducer was placed in the middle and signals were received by a first receiver and a second receiver on opposite sides of the transducer source. FIGS. 16A and 16B illustrate example graphs depicting example sensor readings collected from sensors setup along the pipe and the magnets were distributed azimuthally within the pipe. FIG. 16A illustrates a graph of actionable output from a first differential broadband response signal against magnet perturbation distance for an azimuthal distribution of magnets within an elongated rigid structure, in accordance with one or more implementations. As illustrated, the example graph represents changes in positioning of magnets a magnet perturbation zone. FIG. 16B illustrates a graph of actionable output from a second differential broadband response signal against magnet perturbation distance for an azimuthal distribution of magnets within an elongated rigid structure, in accordance with one or more implementations. The graph illustrates the magnets with respect to the near-neighbor zone. In FIGS. 17A, and 17B, the magnets were distributed axially within the pipe. FIG. 17A illustrates a graph of actionable output from a first differential broadband response signal against magnet perturbation distance for an axial distribution of magnets within an elongated rigid structure, in accordance with one or more implementations. The graph represents the magnets movements with respect to the first receiver. FIG. 17B illustrates a graph of actionable output from a second differential broadband response signal against magnet perturbation distance for an axial distribution of magnets within an elongated rigid structure, in accordance with one or more implementations. The graph illustrates the magnets with respect to the second receiver.

EXAMPLE 7 illustrates the use of narrowband, multi-mode, transmission-reflection, scattering technique.

Example 7

Examples of acoustic large area monitoring of major defects are given below for experiments conducted on the approximately 50-ft-long pipe assembly using magnets that were about ½ inch by about ½ inch by about ⅛ inch. A source transducer was placed in the middle and signals were received by a first receiver and a second receiver on opposite sides of the transducer source. Single-tone Gaussian-enveloped pulses may be used. Delay difference between signal arrivals at the first and second receiver may estimate the location of major defects. FIGS. 18A and 18B illustrate signal traces of 8 azimuthally-placed magnets at 0 feet into the pipe. FIG. 18A illustrates a trace of a first differential narrowband response signal for azimuthal distribution of magnets at a given distance, in accordance with one or more implementations. The signal trace illustrates the signal received from the first receiver. FIG. 18B illustrates a trace of a second differential narrowband response signal for azimuthal distribution of magnets at a given distance, in accordance with one or more implementations. The signal trace illustrates the signal received from the second receiver. Comparing the two signals of FIGS. 18A and 18B may help improve the estimation of the location of major defects in the pipe.

FIGS. 19A and 19B illustrate signal traces of 8 azimuthally-placed magnets at 8 feet into the pipe. FIG. 19A illustrates a trace of a first differential narrowband response signal for azimuthal distribution of magnets at a given distance, in accordance with one or more implementations. The signal trace illustrates the signal received from the first receiver. FIG. 19B illustrates a trace of a second differential narrowband response signal for azimuthal distribution of magnets at a given distance, in accordance with one or more implementations. The signal trace illustrates the signal received from the second receiver. Comparing the two signals of FIGS. 19A and 19B may help improve the estimation of the location of major defects in the pipe.

FIGS. 20A and 20B illustrate signal traces of 8 azimuthally-placed magnets at 16 feet into the pipe. FIG. 20A illustrates a trace of a first differential narrowband response signal for azimuthal distribution of magnets at a given distance, in accordance with one or more implementations. The signal trace illustrates the signal received from the first receiver. FIG. 20B illustrates a trace of a second differential narrowband response signal for azimuthal distribution of magnets at a given distance, in accordance with one or more implementations. The signal trace illustrates the signal received from the second receiver. Comparing the two signals of FIGS. 20A and 20B may help improve the estimation of the location of major defects in the pipe.

FIG. 21A illustrates a time-domain analysis of differential narrowband response signals, comparing the estimated distance and the actual distance of a defect, in accordance with one or more implementations. The time-domain analysis helps illustrate that location estimation improves with perturbation size. With 8 magnet perturbation, accuracy is within 2 feet for the azimuthal case and within 1 foot for the axial case for a 25 foot zone.

FIG. 21B illustrates a signal-intensity analysis of differential narrowband response signals comparing the normalized signal intensity and the actual distance of a defect, in accordance with one or more implementations. The signal-intensity analysis may help estimate distances from smaller distances (e.g. 2-4 feet).

FIG. 21C illustrates a graph of differential narrowband response signals, comparing the estimated distance and the actual distance of one or two defects, in accordance with one or more implementations. The graph illustrates the effectiveness of using narrowband signals for both azimuthally- and axially-distributed magnets, whether small (e.g., about ½ inch by about ½ inch by about ⅛ inch) or large (e.g., about 1 inch by about 1 inch by about ⅛ inch). This could be used to look for reflections from more than one major perturbation within a zone, providing primary and secondary location estimates. The accuracy is within 1.5 feet in a 25 foot zone.

FIG. 15A illustrates a method for detection and monitoring of a mechanical change in an elongated rigid structure, in accordance with one or more implementations. The operations of method 1500 presented below are intended to be illustrative. In some implementations, method 1500 may be accomplished with one or more additional operations not described, and/or without one or more of the operations discussed. Additionally, the order in which the operations of method 1500 are illustrated in FIG. 15 and described below is not intended to be limiting.

In some implementations, method 1500 may be implemented in one or more processing devices (e.g., a digital processor, an analog processor, a physical computer processor, a digital circuit designed to process information, an analog circuit designed to process information, a state machine, and/or other mechanisms for electronically processing information). The one or more processing devices may include one or more devices executing some or all of the operations of method 1500 in response to instructions stored electronically on an electronic storage medium. The one or more processing devices may include one or more devices configured through hardware, firmware, and/or software to be specifically designed for execution of one or more of the operations of method 1500.

An operation 1502 may include locating a first acoustic transducer at a first location along a surface of the rigid structure. The acoustic transducer may be able to generate and obtain acoustic signals. A transducer may convert energy from one form to another, such as turning acoustic energy into an electrical signal, and vice versa. The rigid structure may be a pipe, bridge, railroad, building, airplane, vehicle, and/or other structure.

An operation 1504 may include locating a second acoustic transducer at a second location along the surface of the rigid structure. The second location may be different than the first location.

An operation 1506 may include locating a third acoustic transducer at a third location along the surface of the rigid structure. The second location may be between the first location and the third location. The third location may be different than the first and/or second location. A longitudinal spacing between the first location and the second location may define a first zone. A longitudinal spacing between the second location and the third location may define a second zone.

An operation 1508 may include generating, with the second acoustic transducer, a baseline broadband acoustic signal along the rigid elongated structure. The baseline broadband may be used to compare against subsequent signals to see any changes to the signal. Changes to the signal may imply defects in the rigid elongated structure.

An operation 1510 may include obtaining, with the first acoustic transducer, a first baseline transmission signal responsive to the baseline broadband acoustic signal in the first zone and obtaining, with the third acoustic transducer, a second baseline transmission signal responsive to the baseline broadband acoustic signal in the second zone. The baseline transmissions may be different from the baseline broadband acoustic signal generated by the second acoustic transducer. The differences may result from noise in the rigid structure from reflections of the broadband acoustic signal generated by the second acoustic transducer and/or other noise. Multiple baseline transmission signals may be sent and averaged, or otherwise analyzed, to reduce unwanted noise.

An operation 1512 may include generating, with the second acoustic transducer, a monitoring broadband acoustic signal along the rigid elongated structure. A monitoring broadband acoustic signal may be a signal sent subsequent to the baseline broadband acoustic signal.

An operation 1514 may include obtaining, with the first acoustic transducer, a first monitoring transmission signal responsive to the monitoring broadband acoustic signal in the first zone and obtaining, with the third acoustic transducer, a second monitoring transmission signal responsive to the monitoring transmission signal in the second zone. A monitoring transmission signal may be a signal subsequent to the baseline transmission signal.

An operation 1516 may include determining a first differential transmission signal as a difference between the first monitoring transmission signal and the first baseline transmission signal. The difference may indicate a defect in the rigid structure in the first zone. A defect may include mechanical defects to the structure of the rigid structure, foreign artifacts in the rigid structure, and/or other defects.

An operation 1518 may include determining a second differential transmission signal as a difference between the second monitoring transmission signal and the second baseline transmission signal. The difference may indicate a defect in the rigid structure in the second zone.

An operation 1520 may include determining if the mechanical change occurred in the first zone of the elongated rigid structure based on the first differential transmission signal or if the mechanical change occurred in the second zone of the elongated rigid structure based on the second differential transmission signal.

FIG. 15B illustrates a method for detection and monitoring of a mechanical change in a zone of an elongated rigid structure, in accordance with one or more implementations. An operation 1552 may include generating, with the second acoustic transducer, a baseline narrow-band pulse acoustic signal along the elongated rigid structure. The baseline narrow-band pulse acoustic signal may be used to compare against subsequent signals to see any changes to the signal. The narrow-band pulse acoustic signal may be able to detect subtler changes to the rigid structure than the broadband acoustic signal.

An operation 1554 may include obtaining, with the first acoustic transducer, a first baseline response signal responsive to the baseline narrow-band pulse acoustic signal in the first and second zones and obtaining, with the third acoustic transducer, a second baseline response signal responsive to the baseline narrow-band pulse acoustic signal in the second and first zones. The baseline response signals may be different from the narrow-band pulse acoustic signals generated by the second acoustic transducer. The differences may result from noise in the rigid structure from reflections of the narrow-band pulse acoustic signals generated by the second acoustic transducer and/or other noise. Multiple baseline response signals may be sent and averaged, or otherwise analyzed, to reduce unwanted noise.

An operation 1556 may include generating, with the second acoustic transducer, a monitoring narrow-band pulse acoustic signal along the elongated rigid structure. A monitoring narrow-band pulse acoustic signal may be a signal subsequent to the baseline narrow-band pulse acoustic signal.

An operation 1558 may include obtaining, with the first acoustic transducer, a first monitoring response signal responsive to the baseline narrow-band pulse acoustic signal in the first and second zones and obtaining, with the third acoustic transducer, a second monitoring response signal responsive to the baseline narrow-band pulse acoustic signal in the second and first zones. A monitoring response signal may be a signal subsequent to the baseline response signal. There may be multiple monitoring response signals sent soon after another one, or relatively concurrently.

An operation 1560 may include determining a first differential response signal as a difference between the first monitoring response signal and the first baseline response signal. The difference may indicate a defect in the rigid structure in the first zone. A defect may include mechanical defects to the structure of the rigid structure, foreign artifacts in the rigid structure, and/or other defects.

An operation 1562 may include determining a second differential response signal as a difference between the second monitoring response signal and the second baseline response signal. The difference may indicate a defect in the rigid structure in the second zone.

An operation 1564 may include generating a first differential delay profile as a function of the first differential response signal as compared with the second differential response signal. A first differential delay profile may indicate differences between the first monitoring response signal and the first baseline response signal. The first differential delay profile may help indicate a more particular point within the first zone where the defect is.

An operation 1566 may include generating a second differential delay profile as a function of the second differential response signal as compared with the first differential response signal. A second differential delay profile may indicate finer differences between the second monitoring response signal and the second baseline response signal. The second differential delay profile may help indicate a more particular point within the second zone where the defect is.

An operation 1568 may include determining the relative location of the mechanical change within the first zone or the second zone based on the first differential delay profile and the second differential delay profile.

Embodiments of the present method may be used for monitoring a wide range of engineered structures, such as vessels, pipes, airplanes, railroads, bridges, and buildings.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent component names other than those depicted herein can be applied to the various partitions.

Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the components or functionality described or claimed as part of the component are all configured in a common package. Indeed, any or all of the various components of an component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method for detecting and monitoring a mechanical change in an elongated rigid structure, the method comprising:
   locating a first acoustic transducer at a first location along a surface of the rigid structure;
   locating a second acoustic transducer at a second location along the surface of the rigid structure;
   locating a third acoustic transducer at a third location along the surface of the rigid structure, wherein the second location is between the first location and the third location, a longitudinal spacing between the first location and the second location define a first zone, and a longitudinal spacing between the second location and the third location define a second zone;
   generating, with the second acoustic transducer, a baseline broadband acoustic signal along the rigid elongated structure;
   obtaining, with the first acoustic transducer, a first baseline transmission signal responsive to the baseline broadband acoustic signal in the first zone and obtaining, with the third acoustic transducer, a second baseline transmission signal responsive to the baseline broadband acoustic signal in the second zone;
   generating, with the second acoustic transducer, a monitoring broadband acoustic signal along the rigid elongated structure;
   obtaining, with the first acoustic transducer, a first monitoring transmission signal responsive to the monitoring broadband acoustic signal in the first zone and obtaining, with the third acoustic transducer, a second monitoring transmission signal responsive to the monitoring transmission signal in the second zone;
   determining a first differential transmission signal as a difference between the first monitoring transmission signal and the first baseline transmission signal;
   determining a second differential transmission signal as a difference between the second monitoring transmission signal and the second baseline transmission signal; and
   determining if the mechanical change occurred in the first zone of the elongated rigid structure based on the first differential transmission signal or if the mechanical change occurred in the second zone of the elongated rigid structure based on the second differential transmission signal.

2. The method of claim 1, further comprising:
   generating, with the second acoustic transducer, a baseline narrow-band pulse acoustic signal along the elongated rigid structure;
   obtaining, with the first acoustic transducer, a first baseline response signal responsive to the baseline narrow-band pulse acoustic signal in the first and second zones and obtaining, with the third acoustic transducer, a second baseline response signal responsive to the baseline narrow-band pulse acoustic signal in the second and first zones;
   generating, with the second acoustic transducer, a monitoring narrow-band pulse acoustic signal along the elongated rigid structure;
   obtaining, with the first acoustic transducer, a first monitoring response signal responsive to the monitoring narrow-band pulse acoustic signal in the first and second zones and obtaining, with the third acoustic transducer, a second monitoring response signal responsive to the monitoring narrow-band pulse acoustic signal in the second and first zones;
   determining a first differential response signal as a difference between the first monitoring response signal and the first baseline response signal;
   determining a second differential response signal as a difference between the second monitoring response signal and the second baseline response signal;
   generating a first differential delay profile as a function of the first differential response signal as compared with the second differential response signal;
   generating a second differential delay profile as a function of the second differential response signal as compared with the first differential response signal; and determining the relative location of the mechanical change within the first zone or the second zone based on the first differential delay profile and the second differential delay profile.

3. The method of claim 2, wherein the first and third acoustic transducers each comprise an acoustic sensor configured to detect an acoustic signal.

4. The method of claim 2, wherein the second acoustic transducer comprises an acoustic transmitter configured to generate an acoustic signal.

5. The method of claim 1, further comprising:
normalizing the first monitoring transmission signal to the first baseline transmission signal, whereby maximum values of the first baseline transmission signal and the first monitoring transmission signal are equal to about a first selected value;
performing Short-Time Fourier Transforms of the first baseline and first monitoring transmission signals using a selected time window size, a selected frequency window size, and a selected time step;
calculating a first difference between the Short-Time Fourier Transforms of the first normalized monitoring transmission signal and the first normalized baseline transmission signal, forming thereby a first two-dimensional contour map; and
identifying a first frequency-time mode pair in the first two-dimensional contour map, where one feature of the first frequency-time mode pair has a first maximum positive value and the corresponding feature of the first frequency-time mode pair has a first maximum negative value; and
calculating an amplitude difference between the maximum positive value and the maximum negative value;
determining if the mechanical change occurred in the first zone of the elongated rigid structure based on the amplitude difference.

6. The method of claim 1, further comprising:
normalizing the second monitoring transmission signal to the second baseline transmission signal, whereby maximum values of the second baseline transmission signal and the second monitoring transmission signal are equal to about the first selected value;
performing Short-Time Fourier Transforms of the second baseline and second monitoring transmission signals using the selected time window size, the selected frequency window size, and the selected time step;
calculating a second difference between the Short-Time Fourier Transforms of the second normalized monitoring transmission signal and the second normalized baseline transmission signal, forming thereby a second two-dimensional contour map; and
identifying a second frequency-time mode pair in the second two-dimensional contour map, where one feature of the second frequency-time mode pair has a second maximum positive value and the corresponding feature of the second frequency-time mode pair has a second maximum negative value; and
calculating an amplitude difference between the maximum positive value and the maximum negative value;
determining if the mechanical change occurred in the second zone of the elongated rigid structure based on the amplitude difference.

7. The method of claim 6, further comprising displaying the first and the second two-dimensional contour maps on a graphical user interface.

8. The method of claim 6, further comprising identifying, with a graphical user interface, the selected time window size, the selected frequency window size, and the selected time step.

9. The method of claim 1, wherein the elongated rigid structure comprises metal.

10. The method of claim 1, wherein a size of the first zone is about a size of the second zone.

11. The method of claim 1, wherein the elongated rigid structure comprises a pipe, a pipe assembly, a flange, an elbow, a tee, a reducer, a weld, a vessel, a storage tank, or a storage container.

12. The method of claim 1, further comprising:
generating multiple baseline broadband acoustic signals along the rigid elongated structure;
obtaining multiple first baseline transmission signals responsive to the baseline broadband acoustic signals in the first zone and multiple second baseline transmission signals responsive to the baseline broadband acoustic signals in the second zone;
averaging a selected number of first baseline transmission signals and averaging a selected number of second baseline transmission signals; and
removing DC components from the averaged first baseline transmission signals and the averaged second baseline transmission signals.

13. The method of claim 1, further comprising:
dividing the first and second monitoring transmission signals into a selected number of equal-duration time bins as a function of time;
calculating a cross-correlation function for the first and second monitoring transmission signals and the first and second baseline transmission signals within a time bin;
determining a time shift for the time bins by locating a peak of the cross correlation function;
assigning a value of the first and second monitoring transmission signals to a time bin corresponding to a value of the first or second baseline transmission signals at a corresponding time shifted time bin; and
performing temperature compensation of the monitoring signal using the baseline signal as a comparison signal, thereby generating a temperature-compensated monitoring signal.

14. A method for detecting and monitoring of an anomalous feature in an elongated rigid structure, the method comprising:
locating a first acoustic transducer at a first location along a surface of the rigid structure;
locating a second acoustic transducer at a second location along the surface of the rigid structure;
locating a third acoustic transducer at a third location along the surface of the rigid structure, wherein the second location is between the first location and the third location, a longitudinal spacing between the first location and the second location define a first zone, and a longitudinal spacing between the second location and the third location define a second zone;
generating, with the second acoustic transducer, multiple broadband acoustic signals along the rigid elongated structure, the multiple broadband acoustic signals including a baseline broadband acoustic signal and a monitoring broadband acoustic signal;
obtaining, with the first acoustic transducer and the third acoustic transducer, multiple transmission signals responsive to the multiple broadband acoustic signals, the multiple transmission signals including baseline transmission signals obtained responsive to the baseline broadband acoustic signal and monitoring transmission signals obtained responsive to the monitoring broadband acoustic signal;

determining if an anomalous feature exists in the first zone or the second zone based on a detected change in the monitoring transmission signals from the baseline transmission signals;

generating, with the second acoustic transducer, multiple narrow-band signals along the elongated rigid structure, the multiple narrow-band signals including a baseline narrow-band pulse acoustic signal and a monitoring narrow-band pulse acoustic signal;

obtaining, with the first acoustic transducer, a first baseline response signal responsive to the baseline narrow-band pulse acoustic signal and a first monitoring response signal responsive to the monitoring narrow-band pulse acoustic signal;

obtaining, with the third acoustic transducer, a second baseline response signal responsive to the baseline narrow-band pulse acoustic signal and a second monitoring response signal responsive to the monitoring narrow-band pulse acoustic signal;

generating, with a delay profile generation logical circuit, multiple differential delay profiles as a function of differences between the first and second baseline response signals and the first and second monitoring response signals; and determining the relative location of the mechanical change within the first zone or the second zone based on the differential delay profiles.

15. A method for detecting and monitoring of an anomalous feature in an elongated rigid structure, the method comprising:

locating acoustic transducers at a first location, a second location, and a third location along a surface of the rigid structure, wherein the second location is between the first location and the third location, a longitudinal spacing between the first location and the second location define a first zone, and a longitudinal spacing between the second location and the third location define a second zone;

generating, with one of the acoustic transducers, multiple narrow-band signals along the elongated rigid structure, the multiple narrow-band signals including a baseline narrow-band pulse acoustic signal and a monitoring narrow-band pulse acoustic signal;

obtaining a first baseline response signal responsive to the baseline narrow-band pulse acoustic signal in the first zone and a first monitoring response signal responsive to the monitoring narrow-band pulse acoustic signal in the first zone;

obtaining a second baseline response signal responsive to the baseline narrow-band pulse acoustic signal in the second zone and a second monitoring response signal responsive to the monitoring narrow-band pulse acoustic signal in the second zone;

generating, with a delay profile generation logical circuit, multiple differential delay profiles as a function of differences between the first and second baseline response signals and the first and second monitoring response signals; and determining the relative location of the mechanical change within the first zone or the second zone based on the differential delay profiles.

16. The method of claim 15, wherein obtaining the first and second baseline response signals occurs during a baseline condition in which no detectable anomalous feature is present in either the first zone or the second zone of the elongated rigid structure.

17. The method of claim 15, wherein obtaining the first and second monitoring response signals occurs after obtaining the first and second baseline response signals.

18. The method of claim 15, further comprising:

determining a first differential response signal as a difference between the first monitoring response signal and the first baseline response signal;

determining a second differential response signal as a difference between the second monitoring response signal and the second baseline response signal;

generating a first differential delay profile as a function of the first differential response signal as compared with the second differential response signal; and generating a second differential delay profile as a function of the second differential response signal as compared with the first differential response signal.

19. The method of claim 15, further comprising displaying the differential delay profiles as graphical plots on a graphical user interface.

20. The method of claim 15, wherein the narrow-band acoustic signals comprise Gaussian-enveloped pulses.

* * * * *